United States Patent
Parvulescu et al.

(10) Patent No.: US 9,999,878 B2
(45) Date of Patent: Jun. 19, 2018

(54) TIN-CONTAINING ZEOLITIC MATERIAL HAVING A BEA FRAMEWORK STRUCTURE

(71) Applicant: BASF SE, Ludwigshafen (DE)

(72) Inventors: Andrei-Nicolae Parvulescu, Ruppertsberg (DE); Ulrich Müller, Neustadt (DE); Joaquim H. Teles, Waldsee (DE); Nicolas Vautravers, Mannheim (DE); Georg Uhl, Kaiserslautern (DE); Ive Hermans, Kloten (CH); Patrick Wolf, Donnersdoft (DE); Ceri Hammond, Pontardawe (GB)

(73) Assignee: BASF SE (DE)

( * ) Notice: Subject to any disclaimer, the term of this patent is extended or adjusted under 35 U.S.C. 154(b) by 92 days.

(21) Appl. No.: 15/033,824

(22) PCT Filed: Nov. 5, 2014

(86) PCT No.: PCT/EP2014/073803
§ 371 (c)(1),
(2) Date: May 2, 2016

(87) PCT Pub. No.: WO2015/067654
PCT Pub. Date: May 14, 2015

(65) Prior Publication Data
US 2016/0279621 A1   Sep. 29, 2016

(30) Foreign Application Priority Data

Nov. 5, 2013 (EP) .................................. 13191692

(51) Int. Cl.
| | | |
|---|---|---|
| *C01B 39/06* | (2006.01) | |
| *C01B 39/46* | (2006.01) | |
| *B01J 29/06* | (2006.01) | |
| *B01J 29/89* | (2006.01) | |
| *B01J 29/70* | (2006.01) | |
| *C07D 313/04* | (2006.01) | |
| *B01J 35/00* | (2006.01) | |
| *B01J 35/10* | (2006.01) | |
| *B01J 37/10* | (2006.01) | |
| *B01J 37/30* | (2006.01) | |
| *B01J 29/40* | (2006.01) | |
| *C01B 39/38* | (2006.01) | |
| *C01B 39/02* | (2006.01) | |

(52) U.S. Cl.
CPC ....... *B01J 29/7057* (2013.01); *B01J 29/7007* (2013.01); *B01J 29/89* (2013.01); *B01J 35/002* (2013.01); *B01J 35/1019* (2013.01); *B01J 37/10* (2013.01); *B01J 37/30* (2013.01); *C01B 39/06* (2013.01); *C01B 39/46* (2013.01); *C07D 313/04* (2013.01); *B01J 29/06* (2013.01); *B01J 29/40* (2013.01); *B01J 29/7015* (2013.01); *B01J 29/7038* (2013.01); *B01J 29/7065* (2013.01); *B01J 29/7088* (2013.01); *B01J 2229/183* (2013.01); *B01J 2229/186* (2013.01); *C01B 39/026* (2013.01); *C01B 39/38* (2013.01); *C01P 2002/82* (2013.01)

(58) Field of Classification Search
CPC ....... C01B 39/06; C01B 39/48; C01B 39/026; C01B 39/38; B01J 29/7057; B01J 29/06; B01J 29/89; B01J 2229/16; B01J 2229/183; B01J 2229/186; B01J 37/10; B01J 37/30; C01P 2002/82
See application file for complete search history.

(56) References Cited

FOREIGN PATENT DOCUMENTS

| | | |
|---|---|---|
| EP | 1010667 A1 | 6/2000 |
| WO | WO-2013117537 A1 | 8/2013 |

OTHER PUBLICATIONS

Hammond et al, "Simple and Scalable Preparation of Highly Active Lewis Acidic Sn—B**", Angew. Chem. Int. Ed. (2012) pp. 11736-11739.*
Wolf et al, "Post-synthetic preparation of Sn-, Ti- and Zr-Beta; a facile route to water tolerant, highly active Lewis acidic zeolites", Dalton Trans. (2014) pp. 4514-4519.*
Tang et al, "Improved Postsynthesis Strategy to Sn-Beta Zeolites as Lewis Acid Catalysts for the Ring-Opening Hydration of Epoxides", ACS Catal. (2014) pp. 2801-2810.*
International Search Report with Written Opinion of the International Searching Authority for PCT/EP2014/073803 dated Feb. 6, 2015.
Corma et al., Al-Free Sn-Beta Zeolite as a Catalyst for the Selective Reduction of Carbonyl Compounds (Meerwein-Ponndorf-Verley Reaction), *J. Am. Chem. Soc.*, 2002, vol. 124, pp. 3194-3195.
Corma et al., "Sn-Zeolite Beta as a Heterogeneous Chemoselective Catalyst for Baeyer-Villiger Oxidations", *Nature*, 2001, vol. 412, No. 6845, pp. 423-425.
Database CA; Chemical Abstracts Service, Columbus, OH, Sep. 20, 2012 (Sep. 20, 2012), Kang et al., "Preparation and Characterization of Sn-, Beta, Catalytic Performance for Baeyer-Villiger Oxidation of Cyclohexanone".
Hammond et al., "Simple and Scalable Preparation of Highly Active Lewis Acidic Sn-β", *Angew. Chem. Int. Ed.*, 2012, vol. 51, pp. 11736-11739.

(Continued)

*Primary Examiner* — David M Brunsman
(74) *Attorney, Agent, or Firm* — Drinker Biddle & Reath LLP

(57) ABSTRACT

A process for preparing a tin-containing zeolitic material having a BEA framework structure comprising providing a zeolitic material having a BEA framework structure having vacant tetrahedral framework sites, providing a tin-ion source in solid form, incorporating tin into the zeolitic material via solid-state ion exchange, calcining the zeolitic material, and treating the calcined zeolitic material with an aqueous solution having a pH of at most 5.

26 Claims, No Drawings

(56) References Cited

OTHER PUBLICATIONS

Jones et al., "Synthesis of Hydrophobic Molecular Sieves by Hydrothermal Treatment with Acetic Acid", *Chem. Mater.*, 2001, vol. 13, pp. 1041-1105.
Li et al., "Postsynthesis and Selective Oxidation Properties of Nanosized Sn-Beta Zeolite", *J. Phys. Chem.* C2011, 2011, vol. 115, pp. 3663-3670.

\* cited by examiner

TIN-CONTAINING ZEOLITIC MATERIAL HAVING A BEA FRAMEWORK STRUCTURE

CROSS-REFERENCE TO RELATED APPLICATIONS

This application is a national stage application (under 35 U.S.C. § 371) of PCT/EP2014/073803, filed Nov. 5, 2014, which claims benefit of European Application No. 13191692.6, filed Nov. 5, 2013, both applications of which are incorporated herein by reference in their entirety.

The present invention is directed to a solid-state ion exchange process for preparing a tin-containing zeolitic material having a BEA framework structure. The inventive process comprises providing a zeolitic material having a BEA framework structure having vacant tetrahedral framework sites and further comprises providing a tin-ion source in solid form. In a solid-state ion exchange stage, tin is incorporated into the zeolitic material, and the resulting zeolitic material is calcined. In a post-treatment stage, the thus obtained calcined material is treated with an acidic aqueous solution, which post-treatment stage imparts specific desirable characteristics to the zeolitic material having a BEA framework structure which advantageously differs from the known zeolitic material having a BEA framework structure.

BACKGROUND OF THE INVENTION

Zeolites with the framework structure BEA (zeolite beta) doped with tin have shown promising results if used as catalytically active materials in certain applications such as BaeyerVilliger-type oxidation reactions, isomerization reactions, and the like.

According to the known literature, tin containing zeolites having BEA framework structure BEA are usually prepared by incorporation of tin into the zeolitic framework by hydrothermally treating a zeolitic material having vacant tetrahedral framework sites in the presence of tin-ion source. However, regarding this hydrothermal incorporation of tin, disadvantages have to be taken into account such as long synthesis time periods, the necessity to employ crystallization auxiliaries such as HF or cost intensive templating agents. Still further, only tin containing zeolites having BEA having a low tin content could be obtained.

Hammond et al. describe a process for the preparation of zeolites with the framework structure BEA which are prepared by incorporating tin into the zeolitic framework having vacant tetrahedral framework sites by a specific solid-state ion exchange process wherein said zeolitic framework having vacant tetrahedral framework sites is suitably mixed together with a solid tin-ion source. While the process described in Hammond et al. provides certain advantages compared to the previously known processes for the preparation of tin-containing zeolites having BEA framework structure, the testing of the respectively obtained material in BaeyerVilliger-type oxidation reactions which are explicitly mentioned in Hammond et al. did not show desired selectivities to the reaction product. Further, the process as such included certain reaction steps which, in particular in view of an industrial-scale process for the preparation of a zeolitic BEA framework having vacant tetrahedral framework sites, are not necessarily a realistic option, such as the dealumination via an acid treatment.

DETAILED DESCRIPTION OF THE INVENTION

Therefore, it was an object of the invention to provide tin-containing zeolitic material having a BEA framework structure exhibiting improved characteristics if used as a catalytically active material, in particular if used as catalytically active material in oxidation reactions such as Baeyer-Villiger-type oxidation like the BaeyerVilliger oxidation of cyclic ketones.

Thus, it was a further object of the invention to provide an improved process for the preparation of a tin-containing zeolitic material having a BEA framework structure comprising incorporating tin in a BEA framework structure having vacant tetrahedral sites via a solid-state ion exchange stage.

Surprisingly, it was found that these objections can be achieved by subjecting a zeolitic material having a BEA framework structure which is prepared by incorporating tin in a BEA framework structure having vacant tetrahedral sites via a solid-state ion exchange stage to a specific post-treatment stage.

It was further found that these objects can be achieved by subjecting a zeolitic material having a BEA framework structure to a specific stage during which the vacant tetrahedral framework sites are formed. In this context, it was further found that a certain zeolitic material having a BEA framework structure is specifically suitable.

Therefore, the present invention is directed to a process for preparing a tin-containing zeolitic material having a BEA framework structure comprising (i) providing a zeolitic material having a BEA framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said BEA framework structure having vacant tetrahedral framework sites;

(ii) providing a tin-ion source in solid form;

(iii) incorporating tin into the zeolitic material provided in (i) by bringing the zeolitic material provided in (i) in contact with the tin-ion source provided in (ii) under solid-state ion exchange conditions, obtaining a tin-containing zeolitic material having a BEA framework structure;

(iv) subjecting the zeolitic material obtained from (iii) to a heat treatment;

(v) treating the het-treated zeolitic material obtained from (iv) with an aqueous solution having a pH of at most 5.

As mentioned above, it was found that a specific post-treatment stage allows to prepare advantageous zeolitic materials having a BEA framework structure. This specific post-treatment stage is step (v) of the process of the invention according to which a tin-containing zeolitic material having a BEA framework structure which is prepared by incorporating tin in a BEA framework structure having vacant tetrahedral sites via a solid-state ion exchange stage, is the subjecting of this material to a treatment with an acidic aqueous solution, in particular an aqueous solution having a pH of at most 5. The pH value as referred to in the context of the present invention is to be understood as being determined by the measurement with a pH selective glass electrode.

Step (i)

According to step (i) of the process of the present invention, a zeolitic material is provided having a BEA framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said BEA framework structure having vacant tetrahedral framework sites.

Preferably, the tetravalent element Y is Si. Therefore, the present invention relates to a process wherein according to (i), a zeolitic material is provided having a BEA framework structure comprising $X_2O_3$ and $YO_2$, wherein Y is Si and X is a trivalent element selected from the group consisting of Al, B, In, Ga, Fe, and combinations of two or more thereof, said BEA framework structure having vacant tetrahedral framework sites.

Preferably, the trivalent element X is B. Therefore, the present invention relates to a process wherein according to (i), a zeolitic material is provided having a BEA framework structure comprising $X_2O_3$ and $YO_2$, wherein Y is a tetravalent element selected from the group consisting of Si, Ti, Zr, Ge, and combinations of two or more thereof, and X is B, said BEA framework structure having vacant tetrahedral framework sites.

More preferably, the tetravalent element Y is Si and the trivalent element X is B. Therefore, the present invention relates to a process wherein according to (i), a zeolitic material is provided having a BEA framework structure comprising $X_2O_3$ and $YO_2$, wherein Y is Si and wherein X is B.

Generally, no specific restrictions exist how this zeolitic material having vacant tetrahedral sites is provided. For example, it is conceivable to purchase a suitable, commercially available zeolitic material having vacant tetrahedral sites. Further, for example, any conceivable process for preparing such a zeolitic material can be employed for providing the zeolitic material. For example, it is conceivable to suitably synthesize a zeolitic material having BEA framework structure as a starting zeolitic material from suitable sources of $X_2O_3$ and $YO_2$, either in the presence or in the absence of a suitable template compound, with or without making use of suitable seed crystals, for example in a hydrothermal synthesis process, and subject said starting zeolitic material, after optional washing and/or drying and/or calcining, to a suitable process stage wherein at least a portion of X is removed from the zeolitic framework and the vacant tetrahedral sites are formed. For example, at least a portion of X can be removed from the zeolitic framework by a treatment with steam and/or by a treatment with an acid. For example in Hammond et al., it is described in the experimental section that aluminum is removed from the BEA zeolitic framework by treating the zeolitic material with a 13 M aqueous $HNO_3$ solution. In the context of the present invention, it was found that in particular if X is B, the zeolitic framework having the vacant tetrahedral sites which is used for the subsequent solid-state ion exchange process is advantageously prepared by removing X from the zeolitic framework in a very mild process wherein neither steam nor an acid is used. In particular, it was found that X, preferably B, can be removed by treating the zeolitic starting material with a liquid solvent system, preferably under reflux, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h.

Preferably, according to (i), the zeolitic material having a BEA framework structure having vacant tetrahedral framework sites is provided by a method comprising (i.1) providing a zeolitic starting material having a BEA framework structure, wherein the framework structure of the zeolitic starting material comprises $X_2O_3$ and $YO_2$, preferably $B_2O_3$ and $SiO_2$, and the molar ratio $X_2O_3:YO_2$, preferably $B_2O_3$ and $SiO_2$, is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$, preferably $B_2O_3$ and $SiO_2$, of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h.

Step (i.1)

Generally, there are no specific restrictions how the zeolitic material having a BEA framework structure is provided in (i.1). For example, it may be conceivable to purchase a suitable, commercially available zeolitic material having a BEA framework structure. Further, for example, any conceivable process for synthesizing such a zeolite can be employed for providing the zeolitic material. Preferably, the zeolitic material is provided by a process starting from suitable sources of $X_2O_3$ and $YO_2$ in the presence of a suitable template compound, also referred to as structure directing agent.

Generally, the framework structure of the zeolitic material provided in (i.1) comprises $X_2O_3$ and $YO_2$. Preferably, the suitable sources of $X_2O_3$ and $YO_2$ are employed in an amount so that at least 75 weight-%, more preferably at least 90 weight-%, more preferably at least 95 weight-%, more preferably at least 98 weight-%, more preferably at least 99 weight-% of the framework structure of the zeolitic material provided in (i.1) consist of $X_2O_3$ and $YO_2$.

Generally, $X_2O_3$ and $YO_2$ may be comprised in the zeolitic material having a BEA framework structure with a molar ratio $X_2O_3:YO_2$ of greater than 0.02:1, preferably at least 0.03:1, more preferably in the range of from 0.03:1 to 0.07:1, more preferably from 0.03:1 to 0.06:1, more preferably from 0.03:1 to 0.05:1.

Therefore, a zeolitic material is preferably provided in (i.1), having a BEA framework structure, wherein at least 90 weight-%, more preferably at least 95 weight-%, more preferably at least 98 weight-%, more preferably at least 99 weight-% of the framework structure consists of $B_2O_3$ and $SiO_2$, and wherein the molar ratio $B_2O_3:SiO_2$ is greater than 0.02:1, more preferably at least 0.03:1, more preferably in the range of from 0.03:1 to 0.07:1, more preferably from 0.03:1 to 0.06:1, more preferably from 0.03:1 to 0.05:1. This material is also referred to as B-BEA.

Preferably, the zeolitic material provided in (i.1) is obtained by a synthetic method comprising (i.1.1) preparing a mixture comprising at least one template compound, at least one source for $YO_2$ and at least one source for $X_2O_3$, and (i.1.2) crystallizing the zeolitic material from the mixture prepared in (i.1.1).

According to the present invention, the at least one template compound used in (i.1.1) can be any suitable template compound (structure directing agent). Suitable template compounds include piperidine, hexamethylene imine, N,N,N-trimethyl-1-adamant-ammonium hydroxide, piperidine, hexamethylene imine, dibenzyl-1,4-diaza-bicyclo-[2,2,2]octane, dibenzylmethylammonium, tetraethylammonium hydroxide and a mixture thereof. Preferably, tetraethylammonium hydroxide is used.

Generally, $YO_2$ can be provided in (i.1.1) in any conceivable form, provided that a zeolitic material having a BEA framework structure comprising $YO_2$ can be crystallized in (i.1.2). Preferably, $YO_2$ is provided as such and/or as a compound which comprises $YO_2$ as a chemical moiety and/or as a compound which, partly or entirely, is chemically transformed to $YO_2$ during (i.1.2). Preferably, when Y is Si or a combination of Si with one or more further tetravalent elements, the source for $SiO_2$ provided in (i.1.1) is any conceivable source. Generally, all types of silica and silicates, preferably fumed silica, silica hydrosols, reactive amorphous solid silica, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds can be used.

Preferably, if the mixture according to (i.1.1) comprises at least one source for $SiO_2$, said source comprises at least one compound selected from the group consisting of silica and silicates, preferably silicates, more preferably alkali metal silicates. Among the preferred alkali metal silicates, the at least one source preferably comprises water glass, more preferably sodium and/or potassium silicate, more preferably sodium silicate. More preferably, the source for $SiO_2$ is sodium silicate. Fumed silica may be also preferred.

Generally, $X_2O_3$ can be provided in any conceivable form, provided that a zeolitic material having a BEA framework structure comprising $X_2O_3$ can be crystallized in (i.1.2). Preferably, $X_2O_3$ is provided as such and/or as a compound which comprises $X_2O_3$ as a chemical moiety and/or as a compound which, partly or entirely, is chemically transformed to $X_2O_3$ during the inventive process. Preferably, when X stands for B or for a combination of B with one or more further trivalent elements, for example free boric acid and/or borates and/or boric esters, such as, for example, triethyl borate or trimethyl borate, are used as starting materials and as the at least one source for $X_2O_3$.

Concerning preferred sources of titanium, titanium oxide, titanium halide and tetraalkylorthotitanates may be mentioned. Among these, titanium halides and tetraalkylorthotitanates are more preferred. More preferred are titanium tetrafluoride, tetraethylorthotitanate, tetrapropylorthotitanate, and tetrabutylorthotitanate, with tetrabutylorthotitanate being especially preferred. Concerning preferred sources of zirconium, zirconium oxide, zirconium halides and zirconium tetraalkoxides may be mentioned. Among these, zirconium halides and zirconium tetraalkoxides are more preferred. More preferred are zirconium tetrafluoride, zirconium tetraethoxide, and zirconium tetrabutoxide. Concerning preferred Germanium sources, germanium oxide, germanium chloride, and germanium isopropoxide may be mentioned. Concerning preferred sources of aluminum, alumina, aluminum nitrate may be mentioned, with aluminum nitrate being especially preferred. Concerning preferred sources of indium, indium oxide, indium halides and trialkoxy indium may be mentioned, with indium trichloride, indium trifluoride, and indium triisopropoxide being especially preferred. Concerning preferred sources of gallium, gallium oxide, gallium halides and gallium nitrate may be mentioned, with gallium nitrate, gallium trichloride, and gallium trifluoride being especially preferred. Concerning preferred sources of iron, iron oxide, iron halides, iron acetate and iron nitrate may be mentioned, with iron nitrate being especially preferred.

Generally, the crystallization procedure according to (i.1.2) can be conducted in any conceivable manner, provided that a zeolitic material having a BEA framework structure is crystallized from the mixture according to (i.1.1). The mixture can be crystallized in any type of vessel, wherein a means if agitation is preferably employed, preferably by rotation of the vessel and/or stirring, and more preferably by stirring the mixture.

Preferably, the mixture is heated during at least a portion of the crystallization process in (i.1.2). Generally, the mixture can be heated to any conceivable temperature of crystallization, provided that a zeolitic material having a BEA framework structure is crystallized from the mixture. Preferably, the mixture is heated to a temperature of crystallization in the range of from 80 to 200° C., more preferably from 90 to 190° C., more preferably from 100 to 185° C., more preferably from 120 to 180° C., more preferably from 140 to 175° C., more preferably from 150 to 165° C.

The preferred heating in (i.1.2) of the present invention can be conducted in any conceivable manner suitable for the crystallization of a zeolitic material having a BEA framework structure. Generally, the heating may be conducted at one temperature of crystallization or vary between different temperatures. Preferably, a heating ramp is used for reaching the temperature of crystallization, wherein the heating rate is preferably in the range of from 5 to 100 K/h, more preferably from 10 to 70 K/h, more preferably from 15 to 50 K/h, more preferably from 20 to 30 K/h.

Generally, the duration of the crystallization process in (i.1.2) of the inventive process is not particularly limited. Preferably, the crystallization process is conducted for a period in the range of from 10 to 200 h, more preferably from 20 to 190 h, more preferably from 40 to 170 h, more preferably from 60 to 160 h, more preferably from 80 to 150 h, more preferably from 110 to 130 h.

Preferably, the heating in (i.1.2) is conducted during the entire crystallization process or during only one or more portions thereof, provided that a zeolitic material having the BEA framework structure is crystallized. Preferably, heating is conducted during the entire duration of crystallization.

Preferably, the crystallized material obtained from (i.1.2) is subjected to a sequence of isolation and/or washing steps, wherein the zeolitic material obtained from crystallization in (i.1.2) is preferably subjected to at least one isolation and at least one washing step. Therefore, step (i.1) of the process of the present invention preferably comprises (i.1.1) preparing a mixture comprising at least one template compound, at least one source for $YO_2$ and at least one source for $X_2O_3$, and (i.1.2) crystallizing the zeolitic material from the mixture prepared in (i.1.1);

(i.1.3) isolating and/or washing, preferably isolating and washing the crystallized material obtained from (i.1.2).

Isolation of the crystallized zeolitic material can be achieved by any conceivable method. These methods include, for example, filtration, ultrafiltration, diafiltration and centrifugation and/or decantation methods or, for instance, spray-drying processes and spray granulation processes, wherein filtration methods can involve suction and/or pressure filtration steps. A combination of two or more of these methods can be applied.

For the purpose of isolation, in particular filtration, the pH of the mother liquor obtained from (i.1.2) containing the crystallized zeolitic material is adjusted to a value in the range of from 6 to 9, preferably from 6.5 to 8.5, more preferably from 7 to 8, preferably by adding an acid to the mother liquor, preferably under stirring, wherein the adding of the acid is preferably carried out at a temperature of the mother liquor in the range of from 20 to 70° C., more preferably from 30 to 65° C., more preferably from 40 to 60° C. The acid is preferably an inorganic acid, preferably an aqueous solution containing the inorganic acid, wherein the inorganic acid is preferably selected from the group consisting of phosphoric acid, sulphuric acid, hydrochloric acid, nitric acid, and a mixture of two or more thereof, and wherein the inorganic acid is more preferably nitric acid.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

The crystallized zeolitic material is preferably separated in (i.1.3) from the suspension obtained from (i.1.2) by filtration to obtain a filter cake which is preferably subjected to washing, preferably with water. If washing is applied, it is preferred to continue the washing process until the washing water has a conductivity of at most 1,000 microSiemens/cm, more preferably of at most 850 microSiemens/cm, more preferably of at most 700 microSiemens/cm.

Preferably, the zeolitic material obtained from (i.1.3) is subjected to a heat-treatment stage, wherein the zeolitic material obtained from (i.1.3) is preferably subjected pre-drying and/or drying and/or calcining. Therefore, step (i.1) of the process of the present invention preferably comprises
(i.1.1) preparing a mixture comprising at least one template compound, at least one source for $YO_2$ and at least one source for $X_2O_3$, and
(i.1.2) crystallizing the zeolitic material from the mixture prepared in (i.1.1);
(i.1.3) isolating and/or washing, preferably isolating and washing the crystallized material obtained from (i.1.2);
(i.1.4) subjecting the zeolitic material obtained from (i.1.3) to a heat-treatment stage.

Optionally, the zeolitic material obtained from (i.1.3) is subjected to pre-drying, for example by subjecting the zeolitic material to a suitable gas stream such as air, lean air, or technical nitrogen, for a time preferably in the range of from 4 to 10 h, more preferably from 5 to 8 h.

The optionally the pre-dried filter cake is preferably dried. Preferably, drying is carried out at a temperature in the range of from 100 to 300° C., more preferably from 150 to 275° C., more preferably from 200 to 250° C. in a suitable atmosphere such as technical nitrogen, air, or lean air. Such drying can be accomplished, for example, in a suitable drying oven, or by spray-drying, wherein for spray-drying, a preferably aqueous suspension is preferably prepared from the optionally pre-dried filter cake. If the drying is accomplished by spray-drying, the drying gas inlet temperature is preferably in the range of from 200 to 250° C., more preferably from 220 to 250° C., and the drying gas outlet temperature is preferably in the range of from 100 to 175° C., more preferably from 120 to 150° C.

If spray-drying is carried out, it is conceivable to subject the mother liquor obtained from (i.1.2) containing the zeolitic material, optionally after concentration, directly to spray-drying. Further, it is conceivable to subject the separated and washed zeolitic material to spray-drying, optionally after suitable re-suspending of the washed and optionally pre-dried zeolitic material wherein aqueous suspension are preferably prepared having preferred solids content range of from 2 to 35 weight-%, preferably from 5 to 25 weight-%, more preferably from 10 to 20 weight-%, based on the total weight of the suspension.

Preferably, the heat-treatment according to (i.1.4) comprises calcination of the zeolitic material wherein the zeolitic material is optionally subjected to spray-drying beforehand. Preferably, during calcination, the at least one template compound is at least partially, more preferably essentially removed from the framework structure. The calcination generally involves the heating of the zeolitic material to a temperature of at least 350° C., preferably to a temperature in the range of from 400 to 700° C., more preferably from 450 to 550° C. in a suitable atmosphere such as technical nitrogen, air, or lean air. Preferably, the calcination is carried out for a period in the range of from 1 to 10 h, preferably from 3 to 6 h. Thus, the calcination is preferably carried out at a temperature in the range of from 400 to 700° C., preferably from 450 to 550° C., for a period in the range of from 1 to 10 h, preferably from 3 to 6 h.

Therefore, the present invention relates to the process above, wherein step (i.1) comprises
(i.1.1) preparing a mixture comprising at least one template compound, at least one source for $YO_2$, preferably $SiO_2$, and at least one source for $X_2O_3$, preferably $B_2O_3$;
(i.1.2) crystallizing the zeolitic material having from the mixture prepared in (i.1.1);
(i.1.3) isolating the zeolitic material obtained from (i.1.2) by filtration and washing the isolated zeolitic material;
(i.1.4) subjecting the isolated zeolitic material obtained from (i.1.3) to a heat-treatment stage comprising pre-drying the zeolitic material, re-suspending the pre-dried zeolitic material; spray-drying the suspended zeolitic material, and calcining the spray-dried zeolitic material.

Step (i.2)

According to step (i.2) of the process of the present invention, vacant tetrahedral framework sites are created by treating the zeolitic starting material provided in (i.1) with a liquid solvent system. Preferably, the separated, spray-dried and calcined zeolitic material, provided in (i.1), is subjected to a treatment according to (i.2) with a liquid solvent system wherefrom a zeolitic material having a molar ratio $X_2O_3$:$YO_2$, preferably $B_2O_3$:$SiO_2$, of at most 0.02:1 is obtained.

Generally, no specific restrictions exist concerning the chemical nature of the liquid solvent system used in (i.2). Thus, it is conceivable to use an acidic aqueous system for decreasing the molar ratio $X_2O_3$:$YO_2$, preferably $B_2O_3$:$SiO_2$, of the zeolitic material to a value of at most 0.02:1. As acids, the liquid solvent system may comprise, for example, hydrochloric acid, sulfuric acid, nitric acid, phosphoric acid, formic acid, acetic acid, propionic acid, oxalic acid, or tartaric acid. Preferably, the liquid solvent system used in (i.2) is selected from the group consisting of water, monohydric alcohols, polyhydric alcohols, and mixtures of two or more thereof. Concerning the monohydric alcohols and polyhydric alcohols, no specific restrictions exist. Preferably, these alcohols contain from 1 to 6 carbon atoms, more preferably from 1 to 5 carbon atoms, more preferably from 1 to 4 carbon atoms, and more preferably from 1 to 3 carbon atoms. The polyhydric alcohols preferably comprise from 2 to 5 hydroxyl groups, more preferably from 2 to 4 hydroxyl groups, preferably 2 or 3 hydroxyl groups. Especially preferred monohydric alcohols are methanol, ethanol, and propanol like 1-propanol and 2-propanol. Especially preferred polyhydric alcohols are ethane-1,2-diol, propane-1,2-diol, propane-1,3-diol, propane-1,2,3-triol. If mixtures of two or more of above-described compounds are employed, it is preferred that these mixtures comprise water and at least one monohydric and/or at least one polyhydric alcohol. Most preferably, the liquid solvent system consists of water. Therefore, the present invention relates to above-defined process and zeolitic material obtainable or obtained therefrom, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.

Further, it is especially preferred that the liquid solvent system does not contain an inorganic acid or an organic acid or a salt thereof, the acid being selected from the group consisting of hydrochloric acid, sulfuric acid, nitric acid, phosphoric acid, formic acid, acetic acid, propionic acid, oxalic acid, and tartaric acid. Therefore, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic or organic acid, or a salt thereof, the acid being selected from the group consisting of hydrochloric acid, sulfuric acid, nitric acid, phosphoric acid, formic acid, acetic acid, propionic acid, oxalic acid, and tartaric acid. Even more preferably, the present invention also relates to the process above, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water, and wherein the liquid solvent system does not contain an inorganic or organic acid, or a salt thereof.

The reaction conditions according to (i.2) are not specifically restricted, provided that the solvent system described above is in its liquid state and that the molar ratio $X_2O_3$:$YO_2$, preferably $B_2O_3$:$SiO_2$, is decreased to a value of at most 0.02:1. In particular, concerning the preferred temperatures described below, the skilled person will choose the respective pressure under which the treating is carried out in order to keep the solvent system in its liquid state. Concerning the duration of the treating according to (i.2), no specific restrictions exist. The above mentioned time is to be understood as the time where the liquid solvent system is maintained under the below described treating temperature. Preferably, in (i.2), the treating is carried out for a period of from 6 to 20 h, more preferably from 7 to 17 h, more preferably from 8 to 12 h. The preferred treating temperatures are in the range of from 50 to 125° C., preferably from 90 to 115° C., more preferably from 95 to 105° C. Most preferably, the treating according to (i.2) is carried out at the boiling point of the solvent system. If the solvent system is comprised of two or more components, the treating according to (i.2) is preferably carried out at the boiling point of the component having the lowest boiling point.

Preferably, the treating according to (i.2) is carried out under reflux. Thus, the preferred vessel, representing an open system, used for the treating according to (i.2) is preferably equipped with a reflux condenser. During the treating according to (i.2), the temperature of the liquid solvent system is kept essentially constant or changed, the treating with the liquid solvent system thus being carried out at two or more different temperatures. Most preferably, the temperature is kept essentially constant within the above-defined ranges.

Therefore, the present invention relates to the process above, comprising (i.2) treating the zeolitic material provided in (i.1) with a liquid solvent system, preferably water, thereby obtaining a zeolitic material having a molar ratio $X_2O_3$:$YO_2$, preferably $B_2O_3$:$SiO_2$, of at most 0.02:1 in an open system under reflux at a temperature in the range of from 95 to 105° C., and at least partially separating the zeolitic material from the liquid solvent system.

As far as the amount of zeolitic material which is employed relative to the amount of liquid solvent system, no specific restrictions exist. Preferably, the weight ratio of zeolitic material relative to the liquid solvent system is in the range of from 1:5 to 1:50, more preferably from 1:10 to 1:35, more preferably from 1:10 to 1:20, even more preferably from 1:12 to 1:18.

During treating according to (i.2), it is further preferred to suitably stir the liquid solvent system. During (i.2), the stirring rate is kept essentially constant or changed, the treating thus being carried out at two or more different stirring rates. Most preferably, the zeolitic material is suspended in the liquid solvent system at a first stirring rate, and during (i.2) at the above-described temperatures, the stirring rate is changed, preferably increased. The stirring rates as such can be suitably chosen depending, for example, on the volume of the liquid solvent system, the amount of the zeolitic material employed, the desired temperature, and the like. Preferably, the stirring rate under which the zeolitic material is suspended in the liquid solvent system is in the range of from 5 to 200 r.p.m. (rounds per minute), more preferably from 10 to 200 r.p.m., more preferably from 20 to 55 r.p.m., more preferably from 30 to 50 r.p.m. The stirring rate under which the treating at the above-described temperatures is carried out is preferably in the range of from 50 to 100 r.p.m., more preferably from 55 to 90 r.p.m., more preferably from 60 to 80 r.p.m.

After the treating according to (i.2), the obtained zeolitic material is preferably separated from the liquid solvent system. Therefore, the present invention also relates to the process above, further comprising (i.3) at least partially separating the zeolitic material obtained from (i.2) from the liquid solvent system, optionally including drying.

Step (i.3)

All methods of separating the zeolitic material from the liquid solvent system are conceivable. These methods include, for example, filtration, ultrafiltration, diafiltration and centrifugation methods or, for instance, spray-drying processes and spray granulation processes, wherein filtration methods can involve suction and/or pressure filtration steps. A combination of two or more of these methods can be applied.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol.

Water or a mixture of water and at least one alcohol, preferably water and ethanol, is preferred, distilled water being very particularly preferred as the only washing agent. If washing as applied, it may be preferred to continue the washing process until the washing water has a conductivity of at most 1,000 microSiemens/cm, more preferably of at most 850 microSiemens/cm, more preferably of at most 700 microSiemens/cm.

According to the present invention, the zeolitic material is preferably separated from the suspension by filtration to obtain a filter cake which is preferably subjected to washing, preferably with water.

After separation of the zeolitic material having a BEA framework structure from the liquid solvent system, preferably achieved by filtration, and after washing, the zeolitic material obtained in (ii) is optionally subjected to drying. The drying procedure can optionally comprise one or more drying steps. In general, any conceivable means of drying can be used. Drying procedures preferably include heating and/or applying vacuum to the zeolitic material having a BEA framework structure.

Preferably, the separated and washed zeolitic material is subjected to pre-drying, for example by subjecting the filter cake to a suitable gas stream, such as air, lean air, or nitrogen, for a time preferably in the range of from 4 to 10 h, more preferably from 5 to 8 h.

Preferably, after the optional pre-drying, the zeolitic material is subjected to drying, preferably spray-drying wherein the drying gas inlet temperature is preferably in the range of from 200 to 250° C., more preferably from 220 to 250° C., and the drying gas outlet temperature is preferably in the range of from 100 to 175° C., more preferably from 120 to 150° C. If spray-drying is carried out, it is conceivable to subject the suspension containing the zeolitic material, optionally after concentration, directly to spray-drying. Further, it is conceivable to subject the separated and washed zeolitic material to spray-drying, preferably after suitable re-suspending of the washed and optionally pre-dried zeolitic material, preferably in de-ionized water. Preferably, the solid content of the aqueous suspension is in the range of from 2 to 35 weight-%, preferably from 5 to 25 weight-%, more preferably from 10 to 20 weight-%, based on the total weight of the suspension.

Preferably, the zeolitic material obtained from (i.3) is in the form of a powder, preferably in the form of a spray powder wherein the spray-powder may result either from spray-drying in (i.1) and/or spray-drying in (i.3).

Therefore, according to (i), the zeolitic material having a BEA framework structure having vacant tetrahedral framework sites is preferably provided by a method comprising (i.1) providing a zeolitic starting material having a BEA framework structure, wherein the framework structure of the zeolitic starting material comprises $X_2O_3$ and $YO_2$, preferably $B_2O_3$ and $SiO_2$, and the molar ratio $X_2O_3:YO_2$, preferably $B_2O_3$ and $SiO_2$, is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$, preferably $B_2O_3$ and $SiO_2$, of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, optionally including drying, preferably spray-drying.

According to the present invention, the separated zeolitic material obtained from (i.3) is optionally subjected to calcination in a step (i.4).

Step (i.4)

Preferably, the calcination according to (i.4) is carried out in a suitable atmosphere such as air, lean air, or nitrogen at a temperature in the range of from 400 to 700° C., preferably from 500 to 600° C., for a period in the range of from 1 to 10 h, preferably from 2 to 6 h.

Therefore, according to (i), the zeolitic material having a BEA framework structure having vacant tetrahedral framework sites is preferably provided by a method comprising (i.1) providing a zeolitic starting material having a BEA framework structure, wherein the framework structure of the zeolitic starting material comprises $X_2O_3$ and $YO_2$, preferably $B_2O_3$ and $SiO_2$, and the molar ratio $X_2O_3:YO_2$, preferably $B_2O_3$ and $SiO_2$, is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $X_2O_3:YO_2$, preferably $B_2O_3$ and $SiO_2$, of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, optionally including drying, preferably spray-drying;

(i.4) optionally calcining the separated zeolitic material obtained from (i.3), preferably at a temperature in the range of from 400 to 700° C., more preferably from 450 to 550° C., and preferably for a time period in the range of from 1 to 10 h, more preferably from 3 to 6 h.

Preferably, the zeolitic material obtained in (i.3) is not subjected to calcination prior to (iii).

Therefore, according to (i), the zeolitic material having a BEA framework structure having vacant tetrahedral framework sites is preferably provided by a method comprising (i.1) providing a zeolitic starting material having a BEA framework structure, wherein the framework structure of the zeolitic starting material comprises $X_2O_3$ and $YO_2$, preferably $B_2O_3$ and $SiO_2$, and the molar ratio $X_2O_3$:$YO_2$, preferably $B_2O_3$ and $SiO_2$, is greater than 0.02:1, preferably at least 0.03:1, more preferably in the range of from 0.03:1 to 0.07:1, more preferably from 0.03:1 to 0.06:1, more preferably from 0.03:1 to 0.05:1;

(i.2) creating vacant tetrahedral framework sites by treating the zeolitic starting material provided in (i.1) with a liquid solvent system, preferably under reflux, obtaining a zeolitic material having a molar ratio $X_2O_3$:$YO_2$, preferably $B_2O_3$ and $SiO_2$, of at most 0.02:1, wherein the liquid solvent system is preferably selected from the group consisting of water, methanol, ethanol, propanol, ethane-1,2-diol, propane-1,2-diol, propane-1,3-diol, propane-1,2,3-triol, and mixtures of two or more thereof, the liquid solvent system more preferably being water, wherein more preferably, the liquid solvent system does not contain an inorganic or organic acid, or a salt thereof, and wherein the treating is preferably carried out at a temperature in the range of from 50 to 125° C., more preferably from 90 to 115° C., more preferably from 95 to 105° C., and preferably for a period in the range of from 6 to 20 h, more preferably from 7 to 17 h, more preferably from 8 to 12 h;

(i.3) at least partially separating the zeolitic material obtained from (i.2) from the liquid solvent system, preferably including drying, preferably spray-drying, wherein after (i.3) and before (iii), the preferably dried, more preferably spray-dried zeolitic material is not subjected to calcination at a temperature in the range of from 450 to 550° C. and a time period in the range of from 3 to 6 h, preferably not subjected to calcination at a temperature in the range of from 400 to 700° C. and a time period in the range of from 1 to 10 h, more preferably not subjected to calcination.

According to the present invention, the treatment according to (ii) with the liquid solvent system decreases the molar ratio $X_2O_3$:$YO_2$, preferably $B_2O_3$:$SiO_2$, of the zeolitic material; thus, it is a procedure for removing at least a portion of X from the BEA framework structure and creating vacant tetrahedral sites in the zeolitic framework. Therefore, the molar ratio $X_2O_3$:$YO_2$, preferably $B_2O_3$:$SiO_2$, of the zeolitic material having a BEA framework structure obtained from (ii) is higher than the molar ratio $X_2O_3$:$YO_2$, preferably $B_2O_3$:$SiO_2$, of the zeolitic material having a BEA framework structure provided in (1). According to a preferred embodiment of the present invention, the molar ratio $X_2O_3$:$YO_2$, preferably $B_2O_3$:$SiO_2$, obtained in (ii) is at most 0.02:1, preferably at most 0.01:1, more preferably in the range of from 0.0005:1 to 0.01:1, more preferably from 0.0009:1 to 0.003:1.

Therefore, the present invention relates to the process above, wherein in the framework structure of the zeolitic material provided in (i), the molar ratio $X_2O_3$:$YO_2$, preferably $B_2O_3$:$SiO_2$, is at most 0.02:1, preferably at most 0.01:1, more preferably in the range of from 0.0005:1 to 0.01:1, more preferably from 0.0009:1 to 0.003:1.

According to the present invention, it is preferred to provide a zeolitic material having BEA framework structure based on a $SiO_2$ source and a $B_2O_3$ source. It is especially preferred that the zeolitic material having BEA framework structure is free of aluminum. The term "free of aluminum" as used in this context of the present invention relates to a zeolitic material having BEA framework structure which may contain aluminum only in traces as impurities which may result, for example, from aluminum impurities in the starting materials present in the synthesis mixture used for the preparation of the zeolitic material, that is as impurities in the silicon source, the boron source, the template compound, and the water. In particular, no aluminum source is used in the synthesis mixture in (i.1).

Preferably, at least 95 weight-%, preferably at least 98 weight-%, more preferably at least 99 weight-% of the framework structure of the zeolitic material provided in (i) consist of $X_2O_3$ and $YO_2$, preferably $B_2O_3$ and $SiO_2$. More preferably, at least 99.5 weight-%, more preferably at least 99.8 weight-%, more preferably at least 99.9 weight-% of the framework structure of the zeolitic material provided in (i) consist of $X_2O_3$ and $YO_2$, preferably $B_2O_3$ and $SiO_2$.

Based on the composition of the zeolitic material having BEA framework structure which is subjected to the removal of X, preferably B, from the zeolitic framework, and further based on the composition of the zeolitic material having BEA framework structure obtained from the removal of X, preferably B, from the zeolitic framework, the molar amount of the vacant tetrahedral framework sites formed by the removal stage can be easily calculated.

Step (ii)

According to step (ii) of the process of the present invention, a tin-ion source is provided in solid form.

Generally, there are no specific restrictions regarding the tin-ion source, provided that tin can be incorporated in the zeolitic framework according to (iii) by solid-state ion exchange.

Preferably, the tin-ion source is selected from the group consisting of tin(II) alkoxides, tin(IV) alkoxides, tin(II) salts of organic acids, tin(IV) salts of organic acids, and a mixture a two or more thereof. More preferably, the tin-ion source is selected from the group consisting of tin(II) alkoxides having from 1 to 4 carbon atoms such as 1 carbon atom, 2 carbon atoms, 3 carbon atoms, or 4 carbon atoms, tin(IV) alkoxides having from 1 to 4 carbon atoms such as 1 carbon atom, 2 carbon atoms, 3 carbon atoms, or 4 carbon atoms, tin(II) salts of organic acids having from 1 to 6 carbon atoms such as 1 carbon atom, 2 carbon atoms, 3 carbon atoms, 4 carbon atoms, 5 carbon atoms, or 6 carbon atoms, tin(IV) salts of organic acids having from 1 to 6 carbon atoms such as 1 carbon atom, 2 carbon atoms, 3 carbon atoms, 4 carbon atoms, 5 carbon atoms, or 6 carbon atoms, and a mixture a two or more thereof. More preferably, the tin-ion source includes a tin(II) salt of organic acids having from 1 to 6 carbon atoms such as 1 carbon atom, 2 carbon atoms, 3 carbon atoms, 4 carbon atoms, 5 carbon atoms, or 6 carbon atoms, or a tin(IV) salt of organic acids having from 1 to 6 carbon atoms such as 1 carbon atom, 2 carbon atoms, 3 carbon atoms, 4 carbon atoms, 5 carbon atoms, or 6 carbon atoms. More preferably, the tin-ion source includes a tin(II) salt of organic acids having from 1 to 6 carbon atoms such as 1 carbon atom, 2 carbon atoms, 3 carbon atoms, 4 carbon atoms, 5 carbon atoms, or 6 carbon atoms. More preferably, the tin-ion source includes tin(II) acetate.

Therefore, the present invention relates to the process above, wherein the tin-ion source provided in (ii) is selected from the group consisting of tin(II) alkoxides, tin(IV) alkoxides, tin(II) salts of organic acids, tin(IV) salts of organic acids, and a mixture a two or more thereof, preferably from the group consisting of tin(II) alkoxides having from 1 to 4 carbon atoms, tin(IV) alkoxides having from 1 to 4 carbon atoms, tin(II) salts of organic acids having from 1 to 6, tin(IV) salts of organic acids having from 1 to 6 carbon atoms, and a mixture a two or more thereof, wherein more preferably, the tin-ion source provided in (ii) is tin(II) acetate.

Step (iii)

According to step (iii) of the process of the present invention, tin is incorporated into the zeolitic material provided in (i) by bringing the zeolitic material provided in (i) in contact with the tin-ion source provided in (ii) under solid-state ion exchange conditions, obtaining a tin-containing zeolitic material having a BEA framework structure.

Regarding the amount of the tin-ion source and the amount of the zeolitic material employed in (iii), no specific restrictions exist. Generally, the amount of the tin-ion source will be chosen depending on the desired tin content of the tin-containing zeolitic material which is prepared. Preferably according to the present invention, tin-containing zeolitic material having a high tin content are prepared. Therefore, it is preferred that the tin-ion source is employed in an amount relative to the amount of the zeolitic material having vacant tetrahedral framework sites so that up to 100% of the vacant tetrahedral sites can be filled with tin. Since the molar amount of the vacant tetrahedral framework sites formed by the removal stage can be easily calculated as described above, the necessary amount of the tin-ion source in turn can be easily determined. Preferably, according to (iii), the molar ratio of tin contained in the tin-ion source brought into contact with zeolitic material relative to the vacant tetrahedral framework sites of the zeolitic material is at most 1:1.

Therefore, the present invention relates to the process above, wherein according to (iii), the molar ratio of tin contained in the tin-ion source brought into contact with zeolitic material relative to the vacant tetrahedral framework sites of the zeolitic material is at most 1:1.

Depending on the amount vacant tetrahedral framework sites, preferred tin containing materials are prepared according to the present invention having a tin content in the range of from 2 to 20 weight-%, preferably from 5 to 18 weight-%, more preferably from 8 to 16 weight-%, based on the total weight of the tin-containing zeolitic material.

Regarding the method how the zeolitic material provided in (i) is brought in contact with the tin-ion source provided in (ii) under solid-state ion exchange conditions according to (iii) is not subject to any specific restrictions. Preferably, in (iii), bringing the zeolitic material provided in (i) in contact with the tin-ion source provided in (ii) under solid-state ion exchange conditions comprises mixing the zeolitic material provided in (i) with the tin-ion source.

Any suitable mixing method can be applied. For example, the mixing can be carried out manually or using a suitable mixing apparatus. Manual mixing can be carried, for example, by grinding the zeolitic material provided in (i) together with the tin-ion source provided in (ii), for example in a suitable mortar. Suitable mixing apparatuses include, for example, high energy mixers, grinding mills such as ball mills, rod mills, autogenous mills, semi-autogenous mills, pebble mills, high pressure grinding rolls, buhrstone mills, vertical shaft impactor mills, or tower mills.

Preferably, the mixing is carried out in a suitable apparatus which provides, during mixing, a high energy input, preferably in the range of from 100 to 1,000 W, more preferably from 200 to 800 W, more preferably from 300 to 600 W. If the mixing is carried out in a mixing apparatus which provides the mixing energy by stirring the mixture, it is preferred to carry out the mixing under stirring at a stirring energy input in the range of from 100 to 1000 W, preferably from 200 to 800 W, more preferably from 300 to 600 W.

Preferably, in (iii), the zeolitic material is mixed with the tin-ion source for a time period in the range of from 2 min to 5 h, preferably from 5 min to 3 h, more preferably from 10 min to 2 h.

Therefore, the present invention also relates to the process above, wherein in (iii), tin is incorporated into the zeolitic material provided in (i) by bringing the zeolitic material provided in (i) in contact with the tin-ion source provided in (ii) under solid-state ion exchange conditions, obtaining a tin-containing zeolitic material having a BEA framework structure, said solid-state ion exchange conditions comprising mixing the zeolitic material provided in (i) together with the tin-ion source provided in (ii) at an energy input, preferably provided by stirring the mixture of the zeolitic material provided in (i) and the tin-ion source provided in (ii), in the range of from 100 to 1000 W, preferably from 200 to 800 W, more preferably from 300 to 600 W.

Therefore, the present invention also relates to the process above, wherein in (iii), tin is incorporated into the zeolitic material provided in (i) by bringing the zeolitic material provided in (i) in contact with the tin-ion source provided in (ii) under solid-state ion exchange conditions, obtaining a tin-containing zeolitic material having a BEA framework structure, said solid-state ion exchange conditions comprising mixing the zeolitic material provided in (i) together with the tin-ion source provided in (ii) for a time period in the range of from 2 min to 5 h, preferably from 5 min to 3 h, more preferably from 10 min to 2 h, at an energy input, preferably provided by stirring the mixture of the zeolitic material provided in (i) and the tin-ion source provided in (ii), in the range of from 100 to 1000 W, preferably from 200 to 800 W, more preferably from 300 to 600 W.

According to the process of the present invention, it is possible that prior to mixing the zeolitic material provided in (i) together with the tin-ion source provided in (ii), either the zeolitic material and/or the tin-ion source is grinded or milled separately. Therefore, the present invention also relates to the process above, comprising grinding and/or milling the zeolitic material prior to milling the zeolitic material together with the tin-ion source, or grinding and/or milling the tin-ion source prior to milling the zeolitic material together with the tin-ion source, or grinding and/or milling the zeolitic material prior to milling the zeolitic material together with the tin-ion source and grinding and/or milling the tin-ion source prior to milling the zeolitic material together with the tin-ion source.

Step (iv)

According to step (iv) of the process of the present invention, the zeolitic material obtained from (iii) is subjected to a heat-treatment.

Optionally, said heat treatment comprises drying the zeolitic material obtained from (iii). Such drying can be carried out at a temperature in the range of from 50 to 200° C., preferably from 75 to 175° C., more preferably from 100 to 150° C. Said drying can be carried out for a time period in the range of from 0.5 to 48 h, preferably from 1 to 24 h, more preferably from 2 to 12 h. Further, said drying can be carried out under an atmosphere comprising oxygen, such as pure oxygen, air, or lean air, or under an inert atmosphere such as argon or nitrogen, preferably technical nitrogen. Preferably, said drying is carried out under an atmosphere comprising oxygen.

According to the present invention, it is conceivable that according to step (iv) of the process of the present invention, the zeolitic material obtained from (iii) is subjected to a heat-treatment, which heat-treatment consists of said drying. Therefore, the present invention relates to the process above, wherein according to (iv), the zeolitic material obtained from (iii) is subjected to heat treatment by drying the zeolitic material obtained from preferably at a temperature in the range of from 50 to 200° C., more preferably from 75 to 175° C., more preferably from 100 to 150° C., preferably for a time period in the range of from 0.5 to 48 h, more preferably from 1 to 24 h, more preferably from 2 to 12 h, preferably under an atmosphere comprising oxygen, such as pure oxygen, air, or lean air, or under an inert atmosphere such as argon or nitrogen, preferably technical nitrogen, more preferably under an atmosphere comprising oxygen, such as pure oxygen, air, or lean air.

The drying can be carried out in any suitable apparatus, such as a static oven or in a continuous drying apparatus. The drying can include spray-drying the zeolitic material obtained from (iii), preferably after preparing a preferably aqueous suspension containing the zeolitic material obtained from (iii). Preferably, the solid content of the aqueous suspension is in the range of from 2 to 35 weight-%, preferably from 5 to 25 weight-%, more preferably from 10 to 20 weight-%, based on the total weight of the suspension.

Preferably, according to step (iv) of the process of the present invention, the zeolitic material obtained from (iii) is subjected to a heat-treatment, which heat-treatment comprises calcining the zeolitic material. According to one embodiment of the present invention, the heat treatment according to (iv) consists of calcining the zeolitic material. According to another embodiment of the present invention, the heat treatment according to (iv) comprises drying the zeolitic material obtained from (iii), followed by calcining the dried zeolitic material, wherein it is preferred the that heat treatment according to (iv) consists of drying the zeolitic material obtained from (iii), followed by calcining the dried zeolitic material.

According to the present invention, it is conceivable to carry out the calcining in 1, 2, or more subsequent calcination stages wherein in each stage, the calcination conditions can be the same or different from each other. Preferably, the calcination is carried out in at least one stage in an atmosphere comprising oxygen, such as pure oxygen, air, or lean air. Therefore, it is preferred that the calcining according to (iv) is carried out at least partially in an atmosphere comprising oxygen.

Thus, the heat-treating according to (iv) preferably comprises calcining, wherein the calcining is preferably carried out at a temperature in the range of from 400 to 700° C., more preferably from 450 to 650° C., more preferably from 500 to 600° C., preferably for a time period in the range of from 1 to 10 h, more preferably from 2 to 8 h, more preferably from 3 to 6 hours, preferably at least partially in an atmosphere comprising oxygen, wherein the calcining according to (iv) can be partially carried out in an inert gas atmosphere.

According to a preferred calcination embodiment of the present invention, the calcining according to (iv) is carried out in at least 1 calcination stage wherein in each calcination stage, the calcining is carried out in an atmosphere comprising oxygen. In each of the calcination stages, the calcination temperature is preferably in the range of from 400 to 700° C., more preferably from 450 to 650° C., more preferably from 500 to 600° C., wherein the calcination temperatures in different stages can be different. The overall calcination time of the at least 1 calcination stage is preferably in the range of from 1 to 10 h, more preferably from 2 to 8 h, more preferably from 3 to 6 hours. Preferably, the zeolitic material obtained from (iii) is heated to the calcination temperature at a heating ramp in the range of from 0.2 to 5 K/min, more preferably from 0.5 to 4 K/min, more preferably from 1 to 3 K/min. Preferably, if the calcining according to (iv) is completely carried out in an atmosphere comprising oxygen, it is preferred to carry out the calcining in 1 calcination stage.

Therefore, the present invention relates to the process above wherein according to (iv), the zeolitic material obtained from (iii) is subjected to a heat-treatment, which heat-treatment comprises calcining the zeolitic material in 1 calcination stage, at a calcination temperature preferably in the range of from 400 to 700° C., more preferably from 450 to 650° C., more preferably from 500 to 600° C., for a calcination time preferably in the range of from 1 to 10 h, more preferably from 2 to 8 h, more preferably from 3 to 6 hours, wherein this heat treatment preferably comprises heating the zeolitic material obtained from (iii) to the calcination temperature at a heating ramp in the range of from 0.2 to 5 K/min, more preferably from 0.5 to 4 K/min, more preferably from 1 to 3 K./min.

According to another preferred calcination embodiment of the present invention, the calcining according to (iv) is carried out in at least 2 calcination stages wherein in at least one calcination stage, the calcining is carried out in an atmosphere comprising oxygen, and wherein in at least one calcination stage, the calcining is carried out in an inert atmosphere. In each of the calcination stages, the calcination temperature is preferably in the range of from 400 to 700° C., more preferably from 450 to 650° C., more preferably from 500 to 600° C., wherein the calcination temperatures in different stages can be different. The overall calcination time of the at least 2 calcination stage is preferably in the range of from 1 to 10 h, more preferably from 2 to 8 h, more preferably from 3 to 6 hours. Preferably, the zeolitic material obtained from (iii) is heated to the calcination temperature at a heating ramp in the range of from 0.2 to 5 K/min, more preferably from 0.5 to 4 K/min, more preferably from 1 to 3 K/min. Preferably, if the calcining according to (iv) is carried out in an atmosphere comprising oxygen and in an inert atmosphere, it is preferred to carry out the calcining in 2 calcination stage wherein in the first calcination stage, the calcining is carried out in an atmosphere comprising oxygen and in the second calcination stage, the calcining is carried out in an inert atmosphere, or wherein in the first calcination stage, the calcining is carried out in an inert atmosphere and in the second calcination stage, the calcining is carried out in an atmosphere comprising oxygen.

Therefore, the present invention relates to the process above wherein according to (iv), the zeolitic material obtained from (iii) is subjected to a heat-treatment, which heat-treatment comprises calcining the zeolitic material in 2 calcination stage, at a calcination temperature in each stage preferably in the range of from 400 to 700° C., more preferably from 450 to 650° C., more preferably from 500 to 600° C., for a total calcination time preferably in the range of from 1 to 10 h, more preferably from 2 to 8 h, more preferably from 3 to 6 hours, wherein this heat treatment preferably comprises heating the zeolitic material obtained from (iii) to the calcination temperature at a heating ramp in the range of from 0.2 to 5 K/min, more preferably from 0.5 to 4 K/min, more preferably from 1 to 3 K/min, and wherein in the first calcination stage, the calcining is carried out in an inert atmosphere, preferably nitrogen, and in the second calcination stage, the calcining is carried out in an atmosphere comprising oxygen, preferably air or lean air.

Therefore, the present invention relates to the process above wherein according to (iv), the zeolitic material obtained from (iii) is subjected to a heat-treatment, which heat-treatment comprises calcining the zeolitic material in 2 calcination stage, at a calcination temperature in each stage preferably in the range of from 400 to 700° C., more preferably from 450 to 650° C., more preferably from 500 to 600° C., for a total calcination time preferably in the range of from 1 to 10 h, more preferably from 2 to 8 h, more preferably from 3 to 6 hours, wherein this heat treatment preferably comprises heating the zeolitic material obtained from (iii) to the calcination temperature at a heating ramp in the range of from 0.2 to 5 K/min, more preferably from 0.5 to 4 K/min, more preferably from 1 to 3 K/min, and wherein in the first calcination stage, the calcining is carried out in an atmosphere comprising oxygen, preferably air or lean air, and in the second calcination stage, the calcining is carried out in an inert atmosphere, preferably nitrogen.

The calcining can be carried out in any suitable apparatus, such as a static oven or in a continuous calcining apparatus.

Step (v)

According to step (v) of the process of the present invention, the heat-treated zeolitic material obtained from (iv) is treated with an aqueous solution having a pH of at most 5.

Preferably, the aqueous solution having a pH of at most 5 comprises at least one organic acid, or at least one inorganic acid, or at least one organic acid and at least one inorganic acid. The organic acid is preferably selected from the group consisting of oxalic acid, acetic acid, citric acid, methane sulfonic acid, and a mixture of two or more thereof. The inorganic acid is preferably selected from the group consisting of phosphoric acid, sulphuric acid, hydrochloric acid, nitric acid, and a mixture of two or more thereof. Therefore, the present invention relates to the process above, wherein in (v), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof. More preferably, the aqueous solution comprises an inorganic acid, preferably selected from the group consisting of phosphoric acid, sulphuric acid, hydrochloric acid, nitric acid, and a mixture of two or more thereof. More preferably, the aqueous solution comprises an inorganic acid, preferably selected from the group consisting of phosphoric acid, sulphuric acid, hydrochloric acid, nitric acid, and a mixture of two or more thereof, and does not comprise an organic acid selected from the group consisting of oxalic acid, acetic acid, citric acid, methane sulfonic acid, and a mixture of two or more thereof, more preferably does not contain an organic acid. More preferably, the aqueous solution comprises nitric acid. More preferably, the aqueous solution comprises nitric acid and does not comprise an organic acid selected from the group consisting of oxalic acid, acetic acid, citric acid, methane sulfonic acid, and a mixture of two or more thereof, more preferably does not contain an organic acid. More preferably, the aqueous solution comprises only nitric acid as acidic compound.

Therefore, the present invention also relates to the process above, wherein in (v), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof, the inorganic acid more preferably being nitric acid.

Preferably, in (v), the aqueous solution has a pH in the range of from 0 to 5, preferably from 0 to 4.5, more preferably from 0 to 4, more preferably from 0 to 3.5, more preferably from 0 to 3, more preferably from 0 to 2.5, more preferably from 0 to 2.

Concerning the temperature of the treating with the aqueous solution according to (v), no specific restrictions exist. Preferably, in (v), the heat-treated zeolitic material is treated with the aqueous solution at a temperature in the range of from 20° C. to 130° C., preferably from 50° C. to 120° C., more preferably from 90 to 110° C. While concerning the type of vessel in which the treating in (v) is conducted, no particular restrictions exist, the vessel is suitably chosen to allow to treat zeolitic material at the temperatures described above, at which temperatures the aqueous solution is in its liquid state. Therefore, as far as higher temperatures are concerned, the treating in (v) is carried out in a closed system under autogenous pressure.

Concerning the time period of the treating with the aqueous solution according to (v), no specific restrictions exist. Preferably, in (v), the heat-treated zeolitic material is treated with the aqueous solution for a time period in the range of from 10 min to 40 h, preferably from 30 min to 30 h, more preferably from 1 h to 25 h.

As far as the amount of the aqueous solution used in (v) is concerned, no specific restrictions exist. Preferably, the weight ratio of the aqueous solution relative to the heat-treated zeolitic material is in the range of from 2:1 to 50:1, preferably from 8:1 to 40:1, more preferably from 10:1 to 35:1.

Therefore, the present invention relates to the process above, wherein in (v), the heat-treated zeolitic material obtained from (iv) is treated with an aqueous solution having a pH in the range of from 0 to 5, preferably from 0 to 3.5, more preferably from 0 to 2, at a temperature in the range of from 20° C. to 130° C., preferably from 50° C. to 120° C., more preferably from 90 to 110° C., and for a time period in the range of from 10 min to 40 h, preferably from 30 min to 30 h, more preferably from 1 h to 25 h, wherein the weight ratio of the aqueous solution relative to the heat-treated zeolitic material is in the range of from 2:1 to 50:1, preferably from 8:1 to 40:1, more preferably from 10:1 to 35:1.

During the treating according to (v), it is preferred to suitably stir the aqueous solution containing the zeolitic material. During (v), the stirring rate is kept essentially constant or changed. The stirring rate as such can be suitably chosen depending, for example, on the volume of the aqueous solution, the amount of the zeolitic material employed, the desired temperature, and the like. Preferably, the stirring rate under which the treating at the above-described temperatures is carried out is preferably in the range of from 50 to 300 r.p.m. (rounds per minute), more preferably from 100 to 250 r.p.m., more preferably from 180 to 220 r.p.m.

After treating zeolitic material obtained from (iv) with an aqueous solution having a pH of at most 5 according to (v), it is preferred to separate the tin-containing zeolitic material having a BEA framework structure from the aqueous solution. All conceivable methods of separating the zeolitic material from the aqueous solution are generally possible. These methods include, for example, filtration, ultrafiltration, diafiltration and centrifugation methods or, for instance, spray drying processes and spray granulation processes. A combination of two or more of these methods can be applied. According to a conceivable embodiment of the present invention, the zeolitic material is separated from the aqueous solution by direct spray-drying. Prior to spray-drying, it is possible to increase the zeolitic material content in the aqueous solution by concentrating the suspension or to decrease the zeolitic material content in the aqueous solution by diluting the suspension. Preferably, the zeolitic material is separated from the aqueous solution by a suitable filtration, and the thus obtained material, for example in the form of a filter cake which is optionally subjected to washing.

Either the spray-dried material, is preferably subjected to washing with at least one suitable washing agent. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent. Preferably, the washing is carried out at a temperature of up to 50° C., more preferably in the range of from 15 to 50° C., more preferably from 15 to 35° C., more preferably from 20 to 30° C. Preferably, the washing is carried out until the pH of the water obtained from the washing has a pH in the range of from 6.5 to 7.5, preferably from 6.7 to 7.3, more preferably from 6.9 to 7.1.

Preferably, the optionally washed zeolitic material is subjected to a step (vi) according to which it is dried and/or calcined. More preferably, the optionally washed zeolitic material is subjected to a step (vi) according to which it is dried and calcined.

Step (vi)

Regarding the drying conditions, no specific restrictions exist. Preferably, the drying is carried out at a temperature in the range of from 100 to 180° C., more preferably from 110 to 165° C., more preferably from 120 to 150° C. Preferably, the drying is carried out for a time period in the range of from 10 h to 70 h, more preferably from 12 to 40 h, more preferably from 15 h to 25 h. The drying can be carried out in an atmosphere comprising oxygen such as pure oxygen, air, or lean air, or in an inert atmosphere such as nitrogen or argon, preferably in an atmosphere comprising oxygen, more preferably in air or lean air. The drying can be carried out in a static oven or in a continuous drying apparatus.

Regarding the calcining conditions, no specific restrictions exist. Preferably, the calcining is carried out at a temperature in the range of from 550 to 700° C., preferably from 575 to 690° C., more preferably from 600 to 680° C. Preferably, the calcining is carried out for a time period in the range of from 1 to 10 h, more preferably from 1.5 to 7.5 h, more preferably from 2 to 5 h. The calcining can be carried out in an atmosphere comprising oxygen such as pure oxygen, air, or lean air, or in an inert atmosphere such as nitrogen or argon, preferably in an atmosphere comprising oxygen, more preferably in air or lean air. The calcining can be carried out in a static oven or in a continuous drying apparatus.

Therefore, the present invention relates to the process above, further comprising (vi) drying and/or calcining the zeolitic material obtained from (v), optionally after washing, wherein the drying is preferably carried out at a temperature in the range of from 100 to 180° C., preferably from 120 to 150° C., for a period in the range of from 10 to 70 h, preferably from 15 to 25 h, and calcination is preferably carried out at a temperature in the range of from 550 to 700° C., preferably from 600 to 680° C., for a period in the range of from 1 to 10 h, preferably from 2 to 5 h.

The Tin-Containing Zeolitic Material as Such

According to the present invention, tin-containing zeolites having a BEA framework structure are prepared which, compared to tin-containing zeolites having a BEA framework structure known in the art prepared by solid-state ion exchange, exhibit advantageous characteristics if used as catalytically active materials, preferably in oxidation reactions, in particular in BaeyerVilliger-type oxidation reactions such as the BaeyerVilliger-type oxidation of cyclic ketones. As shown in the examples, it was surprisingly found that the selectivities to the product can be improved significantly by applying the inventive post-treatment stage (v) which, thus, obviously has a significant impact on the chemical and/or physical properties of the zeolitic material which in turn become apparent in said uses.

Therefore, the present invention also relates to a tin-containing zeolitic material having a BEA framework structure, obtainable or obtained by a process as described above, preferably by a process comprising steps (i) to (v), preferably steps (i) to (vi).

Surprisingly, it was found that by applying the inventive post-treatment stage (v), the crystallinity of the zeolitic material obtained from (iv) may be increased, preferably increased for up to 5 percentage points or for up to 10 percentage points or for up to 15 percentage points. Therefore, the present invention also relates to the use of a treatment of a tin-containing zeolitic material having a BEA framework structure, preferably of a tin-containing zeolitic material having a BEA framework structure prepared by solid-state tin ion exchange, for increasing the crystallinity of said tin-containing zeolitic material.

Surprisingly, it was found that by applying the inventive post-treatment stage (v), the hydrophobicity of the zeolitic material obtained from (iv) can be increased. A measure of the hydrophobicity of the zeolitic material is the water uptake of the zeolitic material wherein the higher the water uptake, the lower the hydrophobicity. According to the present invention, it was found that tin-containing zeolitic material having a BEA framework structure can be obtained having a water uptake of at most 12 weight-%, preferably at most 11 weight-%, preferably at most 10 weight-%.

Therefore, the present invention also relates to a tin-containing zeolitic material having a BEA framework structure comprising $X_2O_3$ and $YO_2$, wherein Y is a tetravalent element selected from the group consisting of Si, Ti, Zr, Ge, and combinations of two or more thereof, Y preferably being Si, X is a trivalent element selected from the group consisting of Al, B, In, Ga, Fe, and combinations of two or more thereof. X preferably being B, wherein the framework structure additionally comprises tin, wherein in the framework structure of the zeolitic material, the molar ratio $X_2O_3:YO_2$ is at most 0.02:1, preferably at most 0.01:1, more preferably in the range of from 0.0005:1 to 0.01:1, more preferably from 0.0009:1 to 0.003:1, wherein at least 95 weight-%, preferably at least 98 weight-%, more preferably at least 99 weight-%, more preferably at least 99.5 weight-%, more preferably at least 99.8 weight-%, more preferably at least 99.9 weight-% of the framework structure of the zeolitic material consist of X, Y, O, H, and tin, and wherein the tin-containing zeolitic material has a water uptake of at most 12 weight-%, preferably at most 11 weight-%, preferably at most 10 weight-%.

Preferably, said tin-containing zeolitic material of the present invention have a tin content in the range of from 2 to 20 weight-%, preferably from 5 to 18 weight-%, more preferably from 8 to 16 weight-%, based on the total weight of the tin-containing zeolitic material. Preferred tin contents may be above 10 weight-%, such as in the range of from 11 to 16 weight-% or from 12 to 16 weight-%.

Preferably, said tin-containing zeolitic material of the present invention have a UV/Vis spectrum exhibiting a maximum in the range of from 200 to 220 nm.

Preferably, said tin-containing zeolitic material of the present invention have an XRD spectrum exhibiting peaks at 2theta values at (21.5±0.2)°, (22.6±0.2)°, (25.5±0.2)°, (26.6±0.2)°, (28.8±0.2)°, (29.7±0.2) °, (32.2±0.2) °, (34.0±0.2)°, (37.9±0.2)°. More preferably, said tin-containing zeolitic material of the present invention have an XRD spectrum exhibiting peaks at 2theta values at (21.5±0.2) °, (22.6±0.2)°, (25.5±0.2) °, (26.6±0.2) °, (28.8±0.2)°, (29.7±0.2) °, (32.2±0.2) °, (34.0±0.2)°, (36.1±0.2)°, (37.9±0.1)°, (38.9±0.2) °, (43.7±0.2) °. More preferably, said tin-containing zeolitic material of the present invention have an XRD spectrum exhibiting peaks at 2theta values at (11.7±0.2) °, (13.5±0.2)°, (14.8±0.2) °, (21.5±0.2) °, (22.6±0.2)°, (25.5±0.2) °, (26.6±0.2) °, (28.8±0.2) °, (29.7±0.2) °, (32.2±0.2) °, (34.0±0.2)°, (36.1±0.2)°, (37.9±0.2) °, (38.9±0.2)°, (43.7±0.2)°.

Also, the present invention relates to said tin-containing zeolitic material of the present invention, obtainable or obtained by a process as described above, preferably by a process comprising steps (i) to (v), preferably steps (i) to (vi).

Further, the present invention relates to the use of the tin-containing zeolitic material having a BEA framework structure as described above as a catalytically active material in oxidation reactions, preferably in BaeyerVilliger-type oxidation reactions, more preferably for the BaeyerVilliger oxidation of cyclic ketones.

Yet further, the present invention relates to an oxidation reaction, preferably a BaeyerVilliger-type oxidation reaction, more preferably the BaeyerVilliger oxidation of a cyclic ketone, wherein the tin-containing zeolitic material having a BEA framework structure as described above is employed as a catalytically active material.

Further Process Steps

Generally, it is possible to employ the zeolitic material according to the present invention, present as a zeolitic powder or a zeolitic spray powder, as such, without any further modifications, for example as a catalyst, as a catalyst support, as a molecular sieve, as an adsorbent, as a filler, or the like.

It is also conceivable that based on the zeolitic material of the present invention, a molding is prepared containing the zeolitic material. In such a process, the zeolitic material, optionally after further modification, is suitably shaped and optionally post-treated. Therefore, the present invention also relates to a process as described above, further comprising
(vii) shaping the tin-containing zeolitic material having a BEA framework structure obtained from (v) or (vi), preferably from (vi), obtaining a molding.

For the shaping in (vii), the zeolitic material can be admixed with at least one binder and/or with at least one binder precursor, and optionally with at least one pore-forming agent and/or at least one plasticizing agent.

Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg, Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further conceivable binders might be amphiphilic compounds having a polar and a non-polar moiety and graphite. Further binders might be, for example, clays, such as, for example, montmorillonites, kaolins, metakaoline, hectorite, bentonites, halloysites, dickites, nacrites or anaxites. These binders can be used as such or in the form of suitable precursor compounds which, either during spray-drying and/or the subsequent calcination form the desired binder. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention binders which either completely or partly comprise $SiO_2$, or which are a precursor of $SiO_2$, from which $SiO_2$ is formed, may be preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 m$^2$/g. Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention.

Pore forming agents include, but are not limited to, polymers such as polymeric vinyl compounds, such as polyalkylene oxides like polyethylene oxides, polystyrene, polyacrylates, polymethacrylates, polyolefins, polyamides and polyesters, carbohydrates, such as cellulose or cellulose derivatives like methyl cellulose, or sugars or natural fibers. Further suitable pore forming agents may be, for example, pulp or graphite. If desired with regard to the pore characteristics be achieved, a mixture of two or more pore forming agents may be used. In a particularly preferred embodiment of the process according to the invention, the pore forming agents are removed by calcination according to (viii) and/or (x).

As to the ratio of the amount of the tin-containing zeolitic material relative to the amount of binder used for preparing a molding, it generally can be freely chosen. Generally, the weight ratio of the tin-containing zeolitic material relative to binder is in the range of from 20:1 to 1:20, preferably from 10:1 to 1:10, more preferably from 1:1 to 1:10.

For preparing a molding based on the tin-containing zeolitic material, at last one pasting agent can be used to provide for an improved processability of the moldable mixture. Conceivable pasting agents are, among others, organic, in particular hydrophilic polymers, such as, for example, carbohydrates like cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, carbohydrates such as cellulose, cellulose derivatives, water and mixtures of two or more of these compounds, such as water and cellulose or water and cellulose derivatives are used as pasting agent. In a particularly preferred embodiment of the process according to the invention, the at least one pasting agent is removed by drying and/or calcination, as further described below.

As to the ratio of the amount of tin-containing zeolitic material relative to the amount of pasting agent used for preparing a molding, it generally can be freely chosen. Generally, the weight ratio of the tin-containing zeolitic material relative to binder is in the range of from 20:1 to 1:50, preferably from 10:1 to 1:40, more preferably from 1:1 to 1:30.

Preferably, step (vii) comprises
(vii.1) preparing a mixture comprising the tin-containing zeolitic material having a BEA framework structure and an aqueous solution having a pH of at most 5;
(vii.2) adding a binder or a precursor thereof, preferably a silica binder or a precursor thereof, preferably a pore-forming agent, and optionally a plasticizing agent to the mixture obtained from (vii.1);
(vii.3) subjecting the mixture obtained from (vii.2) to shaping.

The aqueous solution having a pH of at most 5 employed in (vii.1) comprises at least one organic acid, or at least one inorganic acid, or at least one organic acid and at least one inorganic acid. The organic acid is preferably selected from the group consisting of oxalic acid, acetic acid, citric acid, methane sulfonic acid, and a mixture of two or more thereof. The inorganic acid is preferably selected from the group consisting of phosphoric acid, sulphuric acid, hydrochloric acid, nitric acid, and a mixture of two or more thereof. Therefore, the present invention relates to the process above, wherein in (v), the aqueous solution comprises an organic acid, preferably selected from the group consisting of oxalic acid, acetic acid, citric acid, methane sulfonic acid, and a mixture of two or more thereof, and/or comprises an inorganic acid, preferably selected from the group consisting of phosphoric acid, sulphuric acid, hydrochloric acid, nitric acid, and a mixture of two or more thereof. More preferably, the aqueous solution comprises an inorganic acid, preferably selected from the group consisting of phosphoric acid, sulphuric acid, hydrochloric acid, nitric acid, and a mixture of two or more thereof. More preferably, the aqueous solution comprises an inorganic acid, preferably selected from the group consisting of phosphoric acid, sulphuric acid, hydrochloric acid, nitric acid, and a mixture of two or more thereof, and does not comprise an organic acid selected from the group consisting of oxalic acid, acetic acid, citric acid, methane sulfonic acid, and a mixture of two or more thereof, more preferably does not contain an organic acid. More preferably, the aqueous solution comprises nitric acid. More preferably, the aqueous solution comprises nitric acid and does not comprise an organic acid selected from the group consisting of oxalic acid, acetic acid, citric acid, methane sulfonic acid, and a mixture of two or more thereof, more preferably does not contain an organic acid. More preferably, the aqueous solution comprises only nitric acid as acidic compound.

The moldings of the present invention may be shaped in (vii) in every conceivable geometry such as strands, for example having rectangular, triangular hexagonal, quadratic, oval, or circular cross-section, stars, tablets, spheres, hollow cylinders, and the like. Depending on the specific geometry, the shaping process according to (vii) will be chosen. If, according to a preferred embodiment of the present invention, strands are prepared, the shaping according to (vii) preferably comprises extrusion. Suitable extrusion apparatuses are described, for example, in "Ullmann's Enzyklopädie der Technischen Chemie", 4$^{th}$ edition, vol. 2, page 295 et seq., 1972. In addition to the use of an extruder, an extrusion press can also be used for the preparation of the moldings. If necessary, the extruder can be suitably cooled during the extrusion process. Extrusion processes are conceivable wherein per batch, the power consumption is in the range of from 1 to 10 A, preferably from 1.5 to 6 A, more preferably from 2 to 4 A. The strands leaving the extruder via the extruder die head can be mechanically cut by a suitable wire or via a discontinuous gas stream.

The molding obtained from (vii) is optionally dried and/or calcined. No specific restrictions exist concerning the drying and calcination conditions. The drying is preferably carried out at temperatures in the range of in general from 75 to 200° C., preferably from 90 to 170° C., more preferably from 100 to 150° C., and preferably for a duration in the range of from 6 to 24 h, more preferably from 10 to 20 h. The drying can be effected under any suitable gas atmosphere, wherein nitrogen, air and/or lean air are preferred.

The calcination is preferably carried out at temperatures in the range of in general from 400 to 650° C., preferably from 450 to 600° C., more preferably from 475 to 550° C., and preferably for a duration in the range of from 0.25 to 6 h, more preferably from 0.5 to 2 h. The calcination can be effected under any suitable gas atmosphere, wherein air and/or lean air are preferred.

Further, it is conceivable that the moldings comprising the tin-containing zeolitic material are subjected to a treatment with an aqueous system having a pH in the range of 5.5 to 8.

Preferably, the moldings are treated with the aqueous system at a temperature in the range of from 80 to 220° C., preferably from 90 to 210° C., more preferably from 100 to 200° C. Further, the treating with the aqueous system is preferably carried out for a period in the range of from 1 to 20 h, more preferably from 4 to 15 h, more preferably from 6 to 10 h. Preferably, at least 95 weight-%, more preferably at least 99 weight-%, more preferably at least 99.9 weight-% of the aqueous system consists of water. More preferably, the aqueous system is water.

Preferably, the treating with the aqueous system is carried out in a closed system, under autogenous pressure and with or without stirring. According to another embodiment of the present invention, the treating with the aqueous system is carried out in an open system, preferably under reflux, and with or without stirring.

After treating of the moldings with the aqueous system, the moldings are preferably suitably separated from the suspension. All methods of separating the moldings from the suspension are conceivable. These methods include, for example, filtration and centrifugation methods. A combination of two or more of these methods can be applied. According to the present invention, the moldings are preferably separated from the aqueous system by filtration, and the thus obtained moldings are preferably subjected to washing, preferably to washing with water, at a temperature in the range of from up to 50° C., preferably from 15 to 35° C., more preferably from 20 to 30° C.

After treating with the aqueous system, the moldings are preferably subjected to drying and/or calcination, wherein drying is preferably carried out at a temperature in the range of from 100 to 180° C., preferably from 130 to 150° C., for a period in the range of from 10 to 70 h, preferably from 15 to 25 h, and calcination is preferably carried out at a temperature in the range of from 550° C. to 700° C., preferably from 600 to 680° C., for a period in the range of from 1 to 10 h, preferably from 2 to 5 h.

Generally, the present invention further relates to a zeolitic material, optionally contained in a molding, obtainable or obtained by a process according to the present invention.

Further, the present invention relates to a molding, comprising the zeolitic material of the present invention or the zeolitic material obtainable or obtained by the process of the present invention, said molding optionally additionally comprising a binder.

Therefore, the present invention also relates to the process above, further comprising
(vii) shaping the tin-containing zeolitic material having a BEA framework structure obtained from (v) or (vi), preferably from (vi), obtaining a molding;
(viii) drying and/or calcining the molding obtained from (vii);
(ix) optionally subjecting the molding obtained from (vii) or (viii), preferably from (viii), to a water-treatment, wherein the water-treatment comprises treating the molding with liquid water in an autoclave under autogenous pressure at a temperature in the range of from 100 to 200° C.;
(x) optionally drying and/or calcining the water-treated molding obtained from (ix).

Preferably, said stage (vii) comprises
(vii.1) preparing a mixture comprising the tin-containing zeolitic material having a BEA framework structure and an aqueous solution having a pH of at most 5;
(vii.2) adding a binder or a precursor thereof, preferably a silica binder or a precursor thereof, preferably a pore-forming agent, and optionally a plasticizing agent to the mixture obtained from (vii.1);
(vii.3) subjecting the mixture obtained from (vii.2) to shaping.

Further, the present invention relates to the process above, wherein (viii) comprises
(viii.1) drying the molding obtained from (vii) at a temperature in the range of from 75 to 200° C., preferably from 90 to 170° C., more preferably from 100 to 150° C.;
(viii.2) calcining the dried molding obtained from (viii.1) at a temperature in the range of from 400 to 650° C., preferably from 450 to 600° C., more preferably from 475 to 550° C.

Therefore, the present invention also relates to the tin-containing zeolitic material having a BEA framework structure as described above, comprised in a molding, said molding preferably additionally comprising a binder, preferably a silica binder. Further, the present invention also relates to a molding comprising the tin-containing zeolitic material having a BEA framework structure as described above the molding optionally comprising at least one binder, preferably a silica binder. Yet further, the present invention relates to the use of the molding as a catalyst, preferably in oxidation reactions, preferably in BaeyerVilliger-type oxidation reactions; more preferably for the BaeyerVilliger oxidation of cyclic ketones. Also, the present invention relates to an oxidation reaction, preferably a BaeyerVilliger-type oxidation reaction, more preferably the BaeyerVilliger oxidation of a cyclic ketone, wherein the molding as described above, comprising the tin-containing zeolitic material having a BEA framework structure as described above, is employed as a catalyst.

Therefore, the present invention also relates to the use of the tin-containing zeolitic material having a BEA framework structure of the present invention or the use of the moldings of the present invention comprising the tin-containing zeolitic material having a BEA framework structure of the present invention, as a catalyst in a BaeyerVilliger-type oxidation reaction, or to a BaeyerVilliger-type oxidation reaction wherein the tin-containing zeolitic material having a BEA framework structure of the present invention or the moldings of the present invention comprising the tin-containing zeolitic material having a BEA framework structure of the present invention are employed as a catalyst, wherein an organic carbonyl compound according to formula (I) is oxidized, and

(I)

wherein $R_1$ and $R_2$ are independently from one another a linear or branched alkyl residue, a linear or branched alkenyl residue, an aryl or heteroaryl residue, or a hydrogen atom with the proviso that $R_1$ and $R_2$ are not simultaneously a hydrogen atom, said process comprising
(i) reacting the compound of formula (I), optionally in the presence of a solvent, with hydrogen peroxide in the presence of the tin-containing zeolitic material having a BEA framework according to the present invention or the moldings of the present invention comprising the tin-containing zeolitic material having a BEA framework structure of the present invention, preferably at a temperature in the range of from 50 to 150° C., preferably from 70 to 120° C., more preferably from 90 to 110° C., to obtain a compound of formula (II)

(II)

wherein, if neither $R_1$ nor $R_2$ is a hydrogen atom. $R_1$ and $R_2$ may form, together with the carbonyl group or the carboxyl group, a ring and the compound of formula (I) is

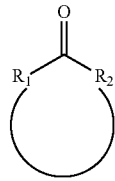

and the compound of formula (II) is

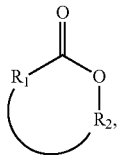

(ii) optionally separating the compound of formula (II) from the mixture obtained in (I); preferably wherein $R_1$ and $R_2$ are independently from one another a linear or branched alkyl residue having from 1 to 20 carbon atoms, a linear or branched alkenyl residue having from 2 to 20 carbon atoms, an aryl or heteroaryl residue having from 4 to 20 carbon atoms, or a hydrogen atom and wherein, if neither $R_1$ nor $R_2$ is a hydrogen atom. $R_1$ and $R_2$ may form, together with the carbonyl group or the carboxyl group, a ring having from 4 to 20 carbon atoms.

The present invention preferably relates to a process for the oxidation of a cyclic ketone of formula (I)

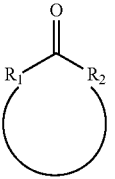

wherein the ring formed by $R_1$, $R_2$, and the carbonyl carbon atom has from 4 to 20, preferably from 4 to 18, more preferably from 5 to 16 carbon, atoms preferably 5, 6, 8, 12, 15 or 16 carbon atoms, said process comprising (i) providing a liquid mixture comprising the compound of formula (I), hydrogen peroxide, at least one at least partially dissolved potassium salt, and optionally a solvent;

(ii) reacting the compound of formula (I) with hydrogen peroxide in the liquid mixture in the presence of a catalyst comprising a tin-containing zeolitic material, obtaining a compound of formula (II)

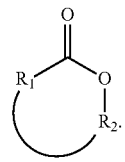

Further, the present invention relates to said use or the said process, wherein the cyclic ketone of formula (I) is selected from the group consisting of cyclopentanone, cyclohexanone, cycloheptanone, cyclooctanone, cyclododecanone, cyclopentadecanone, cyclohexadecanone, 2-pentylcyclopentanone, 2-heptylcyclopentanone, cyclohexadec-8-en-1-one, and a mixture of two or more thereof, the cyclic ketone of formula (I) preferably being cyclohexanone.

The present invention is further illustrated by the following examples and comparative examples.

EXAMPLES

Reference Example 1

Determination of the Water Uptake

Water adsorption/desorption isotherms were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept isothermal during the measurement. The microbalance was calibrated, and the weight of the dried sample was balanced (maximum mass deviation 0.01 weight-%). Water uptake by the sample was measured as the increase in weight over that of the dry sample. First, as adsorption curve was measured by increasing the relative humidity (RH) (expressed as weight-% water in the atmosphere inside of the cell) to which the sample was exposed and measuring the water uptake by the sample as equilibrium. The RH was increased with a step of 10 weight-% from 5% to 85% and at each step the system controlled the RH and monitored the sample weight until reaching the equilibrium conditions after the sample was exposed from 85 weight-% to 5 weight-% with a step of 10% and the change in the weight of the sample (water uptake) was monitored and recorded.

Reference Example 2

Determination of the Crystallinity

The crystallinity of the zeolitic materials according to the present invention was determined by XRD analysis using the EVA method as described in the User Manual DIFFRAC.EVA Version 3, page 105, from Bruker AXS GmbH, Karlsruhe. The respective data were collected on a standard Bruker D8 Advance Diffractometer Series II using a Sol-X detector, from 2° to 50° 2theta, using variable slits (V20), a step size of 0.02° 2theta and a scan speed of 2.4 s/step. Default parameters were used for estimating the background/amorphous content (Curvature=1, Threshold=1).

Reference Example 3

FT-IR Measurements

The FT-IR (Fourier-Transformed-Infrared) measurements were performed on a Nicolet 6700 spectrometer. The powdered material was pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 $cm^{-1}$ region were analyzed and for comparing multiple samples, as reference the band at 1880±5 $cm^{-1}$ was taken,

Reference Example 4

Determination of the Crush Strength of the Moldings of the Present Invention The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given strand as described in Example 5, having a diameter of 1.5 mm, is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 5

Preparation of a Deboronated Zeolitic Material Having a BEA Framework Structure 5.1 Preparing a Boron-Containing Zeolitic Material Having a BEA Framework Structure 209 kg de-ionized water were provided in a vessel. Under stirring at 120 rpm (rounds per minute), 355 kg tetraethylammonium hydroxide were added and the suspension was stirred for 10 minutes at room temperature. Thereafter, 61 kg boric acid were suspended in the water and the suspension was stirred for another 30 minutes at room temperature. Subsequently, 555 kg Ludox® AS-40 were added, and the resulting mixture was stirred at 70 rpm for another hour at room temperature. The liquid gel had a pH of 11.8 as determined via measurement with a pH electrode. The finally obtained mixture was transferred to a crystallization vessel and heated to 160° C. within 6 h under a pressure of 7.2 bar and under stirring (140 rpm). Subsequently, the mixture was cooled to room temperature. The mixture was again heated to 160° C. within 6 h and stirred at 140 rpm for additional 55 h. The mixture was cooled to room temperature and subsequently, the mixture was heated for additional 45 h at a temperature of 160° C. under stirring at 140 rpm. 7800 kg de ionized water were added to 380 kg of this suspension. The suspension was stirred at 70 rpm and 100 kg of a 10 weight-% $HNO_3$ aqueous solution was added. From this suspension the boron containing zeolitic material having a BEA framework structure was separated by filtration. The filter cake was then washed with de-ionized water at room temperature until the washing water had a conductivity of less than 150 microSiemens/cm. The thus obtained filter cake was subjected to pre-drying in a nitrogen stream.

The thus obtained zeolitic material was subjected, after having prepared an aqueous suspension having a solids content of 15 weight-%, based on the total weight of the suspension, using de-ionized water, to spray-drying in a spray-tower with the following spray-drying conditions:
drying gas, nozzle gas: technical nitrogen
temperature drying gas:
    temperature spray tower (in): 235° C.
    temperature spray tower (out): 140° C.
nozzle:
    top-component nozzle supplier Gerig; size 0
    nozzle gas temperature: room temperature
    nozzle gas pressure: 1 bar
operation mode: nitrogen straight
apparatus used: spray tower with one nozzle
configuration: spray tower-filter-scrubber
gas flow: 1,500 kg/h
filter material: Nomex® needle-felt 20 $m^2$
dosage via flexible tube pump: SP VF 15 (supplier: Verder)

The spray tower was comprised of a vertically arranged cylinder having a length of 2,650 mm, a diameter of 1,200 mm, which cylinder was conically narrowed at the bottom. The length of the conus was 600 mm. At the head of the cylinder, the atomizing means (a two-component nozzle) were arranged. The spray-dried material was separated from the drying gas in a filter downstream of the spray tower, and the drying gas was then passed through a scrubber. The suspension was passed through the inner opening of the nozzle, and the nozzle gas was passed through the ring-shaped slit encircling the opening.

The spray-dried material was then subjected to calcination at 500° C. for 5 h. The calcined material had a $B_2O_3$:$SiO_2$ molar ratio of 0.045, a total carbon content of (TOC) 0.08 weight-%, a crystallinity determined by XRD of 56%, and a BET specific surface area determined by DIN 66131 of 498 $m^2/g$.

5.2 Deboronation—Forming Vacant Tetrahedral Sites 840 kg de-ionized water were provided in a vessel equipped with a reflux condenser. Under stirring at 40 rpm, 28 kg of the spray-dried and calcined zeolitic material described above in 5.1 were employed. Subsequently, the vessel was closed and the reflux condenser put into operation. The stirring rate was increased to 70 rpm. Under stirring at 70 rpm, the content of the vessel was heated to 100° C. within 1 h and kept at this temperature for 20 h. Then, the content of the vessel was cooled to a temperature of less than 50° C. The resulting deboronated zeolitic material having a BEA framework structure was separated from the suspension by filtration under a nitrogen pressure of 2.5 bar and washed four times with deionized water at room temperature. After the filtration, the filter cake was dried in a nitrogen stream for 6 h.

The obtained deboronated zeolitic material was subjected, after having re-suspended the zeolitic material in de-ionized water, to spray-drying under the conditions as described in 5.1. The solid content of the aqueous suspension was 15 weight-%, based on the total weight of the suspension. The obtained zeolitic material had a $B_2O_3:SiO_2$ molar ratio of less than 0.002, a water uptake of 15 weight-%, a crystallinity determined by XRD of 48% and a BET specific surface area determined by DIN 66131 of 489 $m^2/g$.

Comparative Example 1

Preparation of a Tin-Containing Zeolitic Material Having a BEA Framework Structure without Acid Treatment 25 g of the deboronated zeolitic material having a BEA framework structure described in Reference Example 5, section 5.2, were added to a mixer (mill type Microton MB550) together with 5.5 g of tin(II) acetate ($Sn(OAc)_2$ [CAS-Nr:638-39-1]), and the mixture was milled for 15 minutes with 14,000 r.p.m. (rounds per minute). After the milling, the mixture was transferred to a porcelain basket and calcined in air at 550° C. for 5 h, with a heating ramp of 2 K/min.

The obtained powder material had a Sn content of 9.6 weight-%, a silicon (Si) content of 38 weight-%, and a TOC of less than 0.1 weight-%. The BET specific surface area measured by DIN 66131 was 423 $m^2/g$, the crystallinity was 51% determined by XRD, and the water uptake was 18 weight-%. The UV/Vis spectrum showed two maxima, one at a wavelength of 200 nm and a second around 250 nm. In the FT-IR spectrum the intensity ratio between a first adsorption band with a maximum between 3701 to 3741 $cm^{-1}$ and a second adsorption with the maximum between 3600 to 3690 $cm^{-1}$ was 1.49.

Comparative Example 2

Preparation of a Tin-Containing Zeolitic Material Having a BEA Framework Structure without Acid Treatment 50 g of the deboronated zeolitic material having a BEA framework structure described in Reference Example 5, section 5.2, were added to a mixer (mill type Microton MB550) together with 14.2 g of tin(II) acetate ($Sn(OAc)_2$ [CAS-Nr:638-39-1]), and the mixture was milled for 15 minutes with 14,000 r.p.m. (rounds per minute). After the milling, the mixture was transferred to a porcelain basket and calcined in air at 500° C. for 3 h, with a heating ramp of 2 K/min.

The obtained powder material had a Sn content of 12.0 weight-%, a silicon (Si) content of 35 wt. % and a TOC of less than 0.1 weight-%. The BET specific surface area measured by DIN 66131 was 391 $m^2/g$, the crystallinity determined by XRD 44%, and the water uptake 15 weight-%. The UV/Vis spectrum showed two maxima, one at wavelength of 200 nm with a shoulder around 250 nm. In the FT-IR spectrum the intensity ratio between a first adsorption band with a maximum between 3701 to 3741 $cm^{-1}$ and a second adsorption with the maximum between 3600 to 3690 $cm^{-1}$ was 1.32.

Comparative Example 3

Preparation of a Tin-Containing Zeolitic Material Having a BEA Framework Structure without Acid Treatment 50 g of the deboronated zeolitic material having a BEA framework structure described in Reference Example 5, section 5.2, were added to a mixer (mill type Microton MB550) together with 14.2 g of tin(II) acetate ($Sn(OAc)_2$ [CAS-Nr:638-39-1]), and the mixture was milled for 15 minutes with 14,000 r.p.m. (rounds per minute). After the milling, the mixture was transferred to a porcelain basket and calcined in air at 500° C. for 3 h under $N_2$ followed by 3 h under air, with a heating ramp of 2 K/min.

The obtained powder material had a Sn content of 13.1 weight-%, a silicon (Si) content of 38 weight-%, and a TOC of less than 0.1 weight-%. The BET specific surface area measured by DIN 66131 was 442 $m^2/g$, the crystallinity determined by XRD 44%, and the water uptake 11.5 weight-%. The UV/Vis spectrum showed two maxima, one at wavelength of 200 nm with a shoulder around 250 nm. In the FT-IR spectrum the intensity ratio between a first adsorption band with a maximum between 3701 to 3741 $cm^{-1}$ and a second adsorption with the maximum between 3600 to 3690 $cm^{-1}$ was 1.62.

Comparative Example 4

Preparation of a Tin-Containing Zeolitic Material Having a BEA Framework Structure without Acid Treatment 50 g of the deboronated zeolitic material having a BEA framework structure described in Reference Example 5, section 5.2, were added to a ball mill (17 balls, total weight of the balls 904 g), together with 14.2 g of tin(II) acetate ($Sn(OAc)_2$ [CAS-Nr:638-39-1]), and the mixture was milled for 15 minutes with 80 r.p.m. (rounds per minute). After the milling, the mixture was transferred to a porcelain basket and calcined in air at 500° C. for 3 h, with a heating ramp of 2 K min.

The obtained powder material had a Sn content of 12.4 weight-%, a silicon (Si) content of 36 weight-%, and a TOC of less than 0.1 weight-%. The BET specific surface area measured by DIN 66131 was 426 $m^2/g$, the crystallinity determined by XRD 42%, and the water uptake 12 weight-%.

Example 1

Preparation of a Tin-Containing Zeolitic Material Having a BEA Framework Structure with Acid Treatment 10 g zeolitic material obtained according to comparative example 1 were provided in a round bottom flask and 300 g of a 30 weight-% $HNO_3$ aqueous solution, having a pH in the range of from 0 to 1, were added. The mixture was stirred at a temperature of 100° C. for a period of 20 h (200 r.p.m.).

The suspension was filtered and the filter cake was then washed with de-ionized water at room temperature until the washing water had a pH of approximately 7.

The obtained zeolitic material was dried at 120° C. for 10 h and calcined by heating to 550° C. (2 K/min) and subsequent heating at 550° C. for 10 h. The dried and calcined zeolitic material had a Si content of 36 weight-%, a Sn content of 9.3 weight-% and a crystallinity determined via XRD of 53%. Further, the zeolitic material had a BET specific surface area, determined according to DIN 66131, of 380 m$^2$/g and a water uptake of 6 weight-%. The UV/Vis spectrum showed two maxima at 208 and 250 nm. In the FT-IR spectrum the intensity ratio between a first adsorption band with a maximum between 3701 to 3741 cm$^{-1}$ and a second adsorption with the maximum between 3600 to 3690 cm$^{-1}$ was 0.93.

Example 2

Preparation of a Tin-Containing Zeolitic Material Having a BEA Framework Structure with Acid Treatment 12 g zeolitic material obtained according to comparative example 2 were provided in a round bottom flask and 360 g of a 30 weight-% HNO$_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7.

The obtained zeolitic material was dried at 120° C. for 10 h and calcined by heating to 550° C. (2 K/min) and subsequent heating at 550° C. for 5 h. The dried and calcined zeolitic material hat a Si content of 37 weight-%, a Sn content of 12.7 weight-%, a TOC of less than 0.1 weight-% and a crystallinity determined via XRD of 48%. Further, the zeolitic material had a BET specific surface area, determined according to DIN 66131, of 395 m$^2$/g and a water uptake of 9 weight-%. The UV/Vis spectrum had a maximum at 208 nm and a shoulder around 257 nm. In the FT-IR spectrum the intensity ratio between a first adsorption band with a maximum between 3701 to 3741 cm$^{-1}$ and a second adsorption with the maximum between 3600 to 3690 cm$^{-1}$ was 1.33, The XRD spectrum of the obtained calcined zeolitic material exhibited the following characteristics:

| 2theta angle/° | d value/Angstrom | Intensity/% |
|---|---|---|
| 11.68 | 7.57 | 13.2 |
| 13.50 | 6.56 | 17.0 |
| 14.77 | 5.99 | 18.3 |
| 21.51 | 4.13 | 38.1 |
| 22.59 | 3.93 | 84.0 |
| 25.52 | 3.49 | 47.5 |
| 26.57 | 3.35 | 87.2 |
| 28.84 | 3.09 | 36.9 |
| 29.69 | 3.01 | 35.7 |
| 32.16 | 2.78 | 33.5 |
| 33.97 | 2.64 | 100 |
| 36.09 | 2.49 | 28.2 |
| 37.90 | 2.37 | 42.6 |
| 38.94 | 2.31 | 28.0 |
| 43.72 | 2.07 | 28.2 |

Example 3

Preparation of a Tin-Containing Zeolitic Material Having a BEA Framework Structure with Acid Treatment 12 g zeolitic material obtained according to comparative example 3 were provided in a round bottom flask and 360 g of a 30 weight-% HNO$_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7.

The obtained zeolitic material was dried at 120° C. for 10 h and calcined by heating to 550° C. (2 K/min) and subsequent heating at 550° C. for 5 h. The dried and calcined zeolitic material hat a Si content of 37 weight-%, a Sn content of 12.6 weight-%, a TOC of less than 0.1 weight-% and a crystallinity determined via XRD of 49%. Further, the zeolitic material had a BET specific surface area, determined according to DIN 66131 of 405 m$^2$/g, and a water uptake of 8.7 weight-%. The UV/Vis spectrum had a maximum at 210 nm and a shoulder around 257 nm. In the FT-IR spectrum the intensity ratio between a first adsorption band with a maximum between 3701 to 3741 cm$^{-1}$ and a second adsorption with the maximum between 3600 to 3690 cm$^{-1}$ was 1.5.

Example 4

Preparation of a Tin-Containing Zeolitic Material Having a BEA Framework Structure with Acid Treatment 900 g of a 30 weight-% HNO$_3$ aqueous solution, having a pH in the range from 0 to 1, were provided in a 2 L stirring apparatus, and 30 g zeolitic material obtained according to comparative example 4 were added. The mixture was stirred at a temperature of 100° C. for a period of 20 h (200 r.p.m.). The suspension was filtered and the filter cake was then washed with de-ionized water at room temperature until the washing water had a pH of approximately 7.

The obtained zeolitic material was dried at 120° C. for 10 h (3 K/min) and calcined in air by heating to 550° C. (2 K/min) and subsequent heating at 550° C. for 10 h. The dried and calcined zeolitic material hat a Si content of 36 weight-%, a Sn content of 12.8 weight-%, a TOC of less than 0.1 weight-% and a crystallinity determined via XRD of 46%. Further, the zeolitic material had a BET specific surface area, determined according to DIN 66131 of 374 m$^2$/g, and a water uptake of 8 weight-%.

Comparative Example 5

Use of the Tin-Containing Zeolitic Material According to Comparative Examples 1 to 4

Baeyer-Villiger Oxidation of Cyclohexanone to Epsilon-Caprolactone in 1,4-Dioxane with an Aqueous Solution of Hydrogen Peroxide Comparative Example 5.1

Use of the Tin-Containing Zeolitic Material According to Comparative Example 1

A 100 mL glass flask was charged with cyclohexanone (1.5 g), the zeolitic material prepared according to comparative example 1 as catalyst (0.1 g, Sn loading=9.6 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 herein below.

Comparative Example 5.2

Use of the Tin-Containing Zeolitic Material According to Comparative Example 2

A 100 mL glass flask was charged with cyclohexanone (1.5 g), the zeolitic material prepared according to comparative example 2 as catalyst (0.1 g, Sn loading=12.0 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

Comparative Example 5.3

Use of the Tin-Containing Zeolitic Material According to Comparative Example 3

A 100 mL glass flask was charged with cyclohexanone (i.5 g), the zeolitic material prepared according to comparative example 3 as catalyst (0.1 g, Sn loading=13.1 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

Comparative Example 5.4

Use of the Tin-Containing Zeolitic Material According to Comparative Example 4

A 100 mL glass flask was charged with cyclohexanone (i.5 g), the zeolitic material prepared according to comparative example 4 as catalyst (0.1 g, Sn loading=12.4 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

Example 5

Use of the Tin-Containing Zeolitic Material According to Examples 1 to 4

Baeyer-Villiger Oxidation of Cyclohexanone to Epsilon-Caprolactone in 1,4-Dioxane with an Aqueous Solution of Hydrogen Peroxide Example 5.1

Use of the Tin-Containing Zeolitic Material According to Example 1

A 100 mL glass flask was charged with cyclohexanone (i.5 g), the zeolitic material prepared according to example 1 as catalyst (0.1 g, Sn loading=9.3 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

Example 5.2

Use of the Tin-Containing Zeolitic Material According to Example 2

A 100 mL glass flask was charged with cyclohexanone (1.5 g), the zeolitic material prepared according to example 2 as catalyst (0.1 g, Sn loading=12.7 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

Example 5.3

Use of the Tin-Containing Zeolitic Material According to Example 3

A 100 mL glass flask was charged with cyclohexanone (i.5 g), the zeolitic material prepared according to example 3 as catalyst (0.1 g, Sn loading=12.6 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

Example 5.4

Use of the Tin-Containing Zeolitic Material According to Example 4

A 100 mL glass flask was charged with cyclohexanone (i.5 g), the zeolitic material prepared according to example 4 as catalyst (0.1 g, Sn loading=12.8 weight-%) and 1,4-dioxane (45 g). The mixture was heated to 95° C. An aqueous solution of hydrogen peroxide (70 weight-%, 0.5 g) was then added, and the reaction mixture was stirred for 4 hours. After cooling down to room temperature, the solution was filtered and the filtrate was analyzed by GC using di-n-butylether as internal standard. The concentrations of epsilon-caprolactone and cyclohexanone in the product mixture were determined by using quantitative GC analysis using di-n-butylether as internal standard. With these data the selectivities to epsilon-caprolactone based on cyclohexanone and hydrogen peroxide and the cyclohexanone conversion were calculated. The results are shown in Table 1 hereinbelow.

TABLE 1

Results of Example 5 and Comparative Example 5

| (Comparative) Example | Selectivity to epsilon-caprolactone based on cyclohexanone/% | Selectivity to epsilon-caprolactone based on $H_2O_2$/% |
| --- | --- | --- |
| Comparative Example 5.1 | 82 | 99 |
| Example 5.1 | 99 | 99 |
| Comparative Example 5.2 | 83 | 99 |
| Example 5.2 | 98 | 99 |
| Comparative Example 5.3 | 82 | 99 |
| Example 5.3 | 91 | 99 |
| Comparative Example 5.4 | 90 | 99 |
| Example 5.4 | 99 | 99 |

These examples and comparative examples clearly show that by subjecting a tin-containing zeolitic material of BEA framework structure which is prepared by solid-state ion exchange to step (v) according to the present invention. i.e. to a treatment with an acidic aqueous solution, the catalytic characteristics with regard to the most important parameter, the selectivity of the zeolitic material, is significantly improved. In particular, while the selectivity to epsilon-caprolactone based on hydrogen peroxide remained constant at the very high level of 99%, the selectivity to epsilon-caprolactone based on the starting material cyclohexanone was increased from 82 to 99% when treating the catalyst according to comparative example 1 according to step (v), from 83 to 98% when treating the catalyst according to comparative example 2 according to step (v), from 82 to 91% when treating the catalyst according to comparative example 3 according to step (v), and from 90 to 99% when treating the catalyst according to comparative example 4 according to step (v).

Example 6

Preparation of a Molding Based on a Tin-Containing Zeolitic Material Having a BEA Framework Structure with Acid Treatment 6.1 Preparing the Zeolitic Material 150 g of deboronated zeolitic material having a BEA framework structure described in Reference Example 5, section 5.2, were added to a mixer (mill type Microton MB550) together with 42.6 g of tin(II) acetate ($Sn(OAc)_2$ [CAS-Nr:638-39-1]), and the mixture was milled for 15 min with 14,000 r.p.m. (rounds per minute). After the milling, the mixture was transferred to a porcelain basket and calcined in air at 500° C. for 3 h, with a heating ramp of 2 K/min. The obtained powder material had a Sn content of 12.0 weight-%, a Si content of 37.0 weight-%, and a TOC of less than 0.1 weight-%. The BET specific surface area measured by DIN 66131 was 464 $m^2/g$, the crystallinity determined by XRD was 51%.

6.2 Acidic Treatment 165 g zeolitic material obtained according to 6.1 above were provided in a round bottom flask and 4,950 g of a 30 weight-% $HNO_3$ aqueous solution, having a pH in the range from 0 to 1, were added. The mixture was stirred at a temperature of 100° C. for a period of 20 h (200 r.p.m.). The suspension was filtered and the filter cake was then washed with de-ionized water at room temperature until the washing water had a pH of approximately 7. The obtained zeolitic material was dried at 120° C. for 10 h and calcined by heating to 550° C. (2 K/min) and subsequent heating at 550° C. for 5 h. The dried and calcined zeolitic material hat a Si content of 37.0 weight-%, a Sn content of 12.4 weight-%, a TOC of less than 0.1 weight-%, and a crystallinity determined via XRD of 62%. Further, the zeolitic material had a BET specific surface area, determined according to DIN 66131 of 391 $m^2/g$.

6.3 Shaping

In a kneader, 34 g of the zeolitic material obtained according to 6.2 above were added and mixed with an acidic solution made from 3.9 g of $HNO_3$ (65 weight-%) dissolved in 15 ml distilled water. The suspension was mixed (kneaded) for 10 min. To the resulting mixture 6.5 g Walocel™ and 108.3 g Ludox® AS-40 were added and mixed for another 30 min. Finally, 45 ml distilled water were added to the mixture and mixed for another 20 min. The paste was then extruded in a Loomis extruder with a pressure (apparatus pressure) of from 100 to 110 bar and an extrudate mass pressure of from 32 to 49 bar. Extrudates of 1.5 mm were obtained and dried in a static oven at 120° C. for 5 h, followed by calcination at 500° C. for 5 h under air and a heating rate of 2 K/min. The calcined extrudates had a bulk density of 535 g/l with a mechanical strength of 11.2 N. The elemental composition was Sn 9.2 weight-%, Si 41 weight-% and a TOC of 0.12 weight-%. Further, the shaped material had a BET specific surface area, determined according to DIN 66131 of 55 m$^2$/g, a water uptake of 8 weight-% and a total pore volume determined by Hg porosimetry according to DIN 66133 of 0.5 ml/g. The UV/Vis spectrum had a maximum at 208 nm and a shoulder around 259 nm. In the FT-IR spectrum the intensity ratio between a first adsorption band with a maximum between 3701 to 3741 cm$^{-1}$ and a second adsorption with the maximum between 3600 to 3690 cm$^{-1}$ was 3.3.

CITED LITERATURE

Hammond C., et al., Simple and Scalable Preparation of Highly Active Lewis Acidic Sn-beta; Angw. Chem. Int. Ed. 2012 (51), pp. 11736-11739

The invention claimed is:
1. A process for preparing a tin-containing zeolitic material having a BEA framework structure comprising
  (i) providing a zeolitic material having a BEA framework structure comprising $X_2O_3$ and $YO_2$, wherein Y is a tetravalent element selected from the group consisting of Si, Ti, Zr, Ge, and combinations of two or more thereof, and X is a trivalent element selected from the group consisting of Al, B, In, Ga, Fe, and combinations of two or more thereof, said BEA framework structure having vacant tetrahedral framework sites;
  (ii) providing a tin-ion source in solid form;
  (iii) incorporating tin into the zeolitic material provided in (i) by contacting the zeolitic material with the tin-ion source under solid-state ion exchange conditions;
  (iv) subjecting the zeolitic material obtained from (iii) to a heat treatment;
  (v) treating the heat-treated zeolitic material with an aqueous solution having a pH of at most 5.
2. The process of claim 1, wherein Y is Si and X is B.
3. The process of claim 1, wherein the zeolitic material having a BEA framework structure with vacant tetrahedral framework sites according to (i) is produced by a process comprising:
  (i.1) providing a zeolitic starting material having a BEA framework structure, wherein the framework structure of the zeolitic starting material comprises $X_2O_3$ and $YO_2$ and the molar ratio $X_2O_3:YO_2$ is in a range of from 0.03:1 to 0.07:1;
  (i.2) creating vacant tetrahedral framework sites by treating the zeolitic starting material provided in (i.1) with a liquid solvent system, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, and the treating is carried out at a temperature in a range of from 50 to 125° C.;
  (i.3) at least partially separating the zeolitic material obtained from (i.2) from the liquid solvent system, and optionally drying the separated zeolitic material;
  (i.4) optionally calcining the separated zeolitic material at a temperature in a range of from 400 to 700° C.
4. The tin-containing zeolitic material obtainable or obtained by a process according to claim 3.
5. The process of claim 1, wherein in the framework structure of the zeolitic material a molar ratio $X_2O_3:YO_2$ is in a range of from 0.01:1.

6. The process of claim 1, wherein the framework structure of the zeolitic material consists of at least 98 weight-% of $X_2O_3$ and $YO_2$.
7. The process of claim 1, wherein the tin-ion source is selected from the group consisting of tin(II) alkoxides, tin(IV) alkoxides, tin(II) salts of organic acids, tin(IV) salts of organic acids, and a mixture a two or more thereof.
8. The process of claim 7, wherein the tin(II) alkoxides have from 1 to 4 carbon atoms, the tin(IV) alkoxides have from 1 to 4 carbon atoms, the tin(II) salts of organic acids have from 1 to 6 carbon atoms, the tin(IV) salts of organic acids have from 1 to 6 carbon atoms.
9. The process of claim 1, wherein the molar ratio of tin to the vacant tetrahedral framework sites of the zeolitic material is at most 1:1.
10. The process of claim 1, wherein the contacting of the zeolitic material includes mixing of the zeolitic material with the tin-ion source.
11. The process of claim 10, wherein the mixing is carried out under stirring at a stirring energy input min the range of from 100 to 1000 W.
12. The process of claim 10, further comprising grinding and/or milling the zeolitic material prior to mixing the zeolitic material together with the tin-ion source, or grinding and/or milling the tin-ion source prior to mixing the zeolitic material together with the tin-ion source, or grinding and/or milling the zeolitic material prior to mixing the zeolitic material together with the tin-ion source and grinding and/or milling the tin-ion source prior to mixing the zeolitic material together with the tin-ion source.
13. The process of claim 1, wherein the heat-treating includes calcining, wherein the calcining is carried out at a temperature in a range of from 400 to 700° C., at least partially in an atmosphere comprising oxygen.
14. The process of claim 1, wherein in (v), the aqueous solution comprises an organic acid selected from the group consisting of oxalic acid, acetic acid, citric acid, methane sulfonic acid, and a mixture of two or more thereof, or the aqueous solution comprises an inorganic acid selected from the group consisting of phosphoric acid, sulphuric acid, hydrochloric acid, nitric acid, and a mixture of two or more thereof, or a mixture of the organic acid and the inorganic acid.
15. The process of claim 14, wherein the aqueous solution has a pH in the range of from 0 to 2.
16. The process of claim 1, wherein in (v), the heat-treated zeolitic material is treated with the aqueous solution at a weight ratio of the aqueous solution relative to the heat-treated zeolitic material in a range of from 2:1 to 50:1.
17. The process of claim 1, further comprising
  (vi) drying and/or calcining the zeolitic material obtained from (v), optionally after washing, wherein the drying is carried out at a temperature in the range of from 100 to 180° C., and calcination is carried out at a temperature in the range of from 550 to 700° C.
18. The process of claim 17, further comprising
  (vii) shaping the tin-containing zeolitic material having a BEA framework structure obtained from (v) or (vi), to provide a molding;
  (viii) drying and/or calcining the molding obtained from (vii);
  (ix) optionally subjecting the molding obtained from (vii) or (viii), to a water-treatment, wherein the water-treatment comprises treating the molding with liquid water in an autoclave under autogenous pressure at a temperature in a range of from 100 to 200° C.;

(x) optionally drying and/or calcining the water-treated molding obtained from (ix).

19. The process of claim 18, wherein (vii) comprises
(vii.1) preparing a mixture comprising the tin-containing zeolitic material having a BEA framework structure and an aqueous solution having a pH of at most 5;
(vii.2) adding a binder or a precursor thereof, and optionally a pore-forming agent, and optionally a plasticizing agent to the mixture obtained from (vii.1);
(vii.3) subjecting the mixture obtained from (vii.2) to shaping.

20. The process of claim 19, wherein (viii) comprises
(viii.1) drying the molding obtained from (vii) at a temperature in the range of from 75 to 200° C.; and
(viii.2) calcining the dried molding obtained from (viii.1) at a temperature in the range of from 400 to 650° C.

21. A tin-containing zeolitic material having a BEA framework structure comprising $X_2O_3$ and $YO_2$, wherein Y is a tetravalent element selected from the group consisting of Si, Ti, Zr, Ge, and combinations of two or more thereof X is a trivalent element selected from the group consisting of Al, B, In, Ga, Fe, and combinations of two or more thereof, wherein the framework structure additionally comprises tin, wherein in the framework structure of the zeolitic material, the molar ratio $X_2O_3:YO_2$, is at most 0.02:1, wherein at least 95 weight-% of the framework structure of the zeolitic material consist of X, Y, O, H, and tin, and wherein the tin-containing zeolitic material has a water uptake of at most 12 weight-%.

22. The tin-containing zeolitic material of claim 21, having a tin content in a range of from 5 to 18 weight-%, based on the total weight of the tin-containing zeolitic material.

23. The tin-containing zeolitic material of claim 21, having a UV/Vis spectrum exhibiting a maximum in the range of from 200 to 220 nm.

24. The tin-containing zeolitic material of claim 23, having an XRD spectrum exhibiting peaks at 2theta values at (21.5±0.2)°, (22.6±0.2)°, (25.5±0.2)°, (26.6±0.2)°, (28.8±0.2)°, (29.7±0.2)°, (32.2±0.2)°, (34.0±0.2)°, and (37.9±0.2)°.

25. A process for the oxidation of cyclic ketones, the process comprising contacting the cyclic ketones with the tin-containing zeolitic material having a BEA framework structure according to claim 21 to provide a Baeyer Villiger oxidation of the cyclic ketones.

26. A molding comprising the tin-containing zeolitic material having a BEA framework structure according to claim 21, and a binder, the molding present as a catalyst for the BaeyerVilliger oxidation of cyclic ketones.

* * * * *